United States Patent
Uehara et al.

(10) Patent No.: US 11,925,108 B2
(45) Date of Patent: Mar. 5, 2024

(54) COMPOUND HAVING TRIARYLAMINE STRUCTURE AND ORGANIC ELECTROLUMINESCENCE DEVICE

(71) Applicant: HODOGAYA CHEMICAL CO., LTD., Tokyo (JP)

(72) Inventors: Takuya Uehara, Tokyo (JP); Kouki Kase, Tokyo (JP); Kyung-Hwa Park, Tokyo (JP); Yuta Hirayama, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 599 days.

(21) Appl. No.: 17/057,040

(22) PCT Filed: Jun. 20, 2019

(86) PCT No.: PCT/JP2019/024590
§ 371 (c)(1),
(2) Date: Nov. 19, 2020

(87) PCT Pub. No.: WO2020/004235
PCT Pub. Date: Jan. 2, 2020

(65) Prior Publication Data
US 2021/0210693 A1    Jul. 8, 2021

(30) Foreign Application Priority Data

Jun. 25, 2018 (JP) ................. 2018-120071

(51) Int. Cl.
*C07C 211/54* (2006.01)
*C07C 211/58* (2006.01)
(Continued)

(52) U.S. Cl.
CPC .......... *H10K 85/631* (2023.02); *C07C 211/54* (2013.01); *C07C 211/58* (2013.01);
(Continued)

(58) Field of Classification Search
None
See application file for complete search history.

(56) References Cited

U.S. PATENT DOCUMENTS

| | | |
|---|---|---|
| 5,639,914 A | 6/1997 | Tomiyama et al. |
| 5,792,557 A | 8/1998 | Nakaya et al. |

(Continued)

FOREIGN PATENT DOCUMENTS

| | | | | |
|---|---|---|---|---|
| CN | 104844475 A | * | 8/2015 | ........... C07C 255/42 |
| CN | 105655492 A | | 6/2016 | |

(Continued)

OTHER PUBLICATIONS

Machine translation of CN-104844475, translation generated Apr. 2023, 7 pages. (Year: 2023).*

(Continued)

*Primary Examiner* — Robert S Loewe
(74) *Attorney, Agent, or Firm* — Birch, Stewart, Kolasch & Birch, LLP

(57) ABSTRACT

An object of the present invention is to provide an organic compound that has excellent properties, with excellent hole injection and transport performance, electron blocking capability, and high stability in a thin film state, and furthermore to provide a highly efficient and highly durable organic EL device by using this compound. The present invention relates to a compound having a triarylamine structure and being represented by the structural formula (A-1) below, where A, B, and C may be the same or different, and each represent a group represented by the structural formula (B-1) below, a substituted or unsubstituted aromatic hydrocarbon group, a substituted or unsubstituted aromatic heterocyclic group, or a substituted or unsubstituted fused polycyclic aromatic group, where at least one of A, B, and C is not the group represented by the structural formula (B-1) below.

(Continued)

(For the symbols and the like in the formulae, see the descriptions in the specification.)

7 Claims, 1 Drawing Sheet

(51) Int. Cl.
| | | |
|---|---|---|
| *C07C 211/61* | (2006.01) | |
| *H10K 85/60* | (2023.01) | |
| *H10K 50/11* | (2023.01) | |
| *H10K 50/15* | (2023.01) | |
| *H10K 50/17* | (2023.01) | |
| *H10K 50/18* | (2023.01) | |

(52) U.S. Cl.
CPC .......... *C07C 211/61* (2013.01); *H10K 85/633* (2023.02); *H10K 50/11* (2023.02); *H10K 50/15* (2023.02); *H10K 50/17* (2023.02); *H10K 50/18* (2023.02)

(56) References Cited

U.S. PATENT DOCUMENTS

| | | |
|---|---|---|
| 7,799,492 B2 | 9/2010 | Abe et al. |
| 8,021,764 B2 | 9/2011 | Hwang et al. |
| 2004/0263067 A1 | 12/2004 | Saitoh et al. |
| 2011/0031877 A1 | 2/2011 | Takada et al. |
| 2013/0214263 A1 | 8/2013 | Yase et al. |
| 2015/0270506 A1* | 9/2015 | Voges .................... H10K 50/11 257/40 |
| 2016/0099420 A1 | 4/2016 | Itoi et al. |
| 2016/0126469 A1 | 5/2016 | Nakano |
| 2016/0141509 A1 | 5/2016 | Fuchiwaki et al. |
| 2016/0155943 A1 | 6/2016 | Sasaki et al. |
| 2016/0190464 A1* | 6/2016 | Lim ..................... C07D 307/91 257/40 |
| 2016/0365517 A1 | 12/2016 | Mun et al. |
| 2017/0012212 A1 | 1/2017 | Lee et al. |
| 2017/0062728 A1 | 3/2017 | Mun et al. |
| 2017/0373254 A1* | 12/2017 | Lee .................... H10K 85/6572 |
| 2019/0185412 A1* | 6/2019 | Xia ....................... C07C 211/61 |
| 2020/0335703 A1* | 10/2020 | Mochizuki ........... H10K 85/631 |

FOREIGN PATENT DOCUMENTS

| | | |
|---|---|---|
| CN | 106831313 A | 6/2017 |
| CN | 108101898 A | 6/2018 |
| CN | 109206327 A | 1/2019 |
| CN | 109485577 A | 3/2019 |
| EP | 2 684 932 A1 | 1/2014 |
| JP | 2005-15418 A | 1/2005 |
| JP | 2010-186983 A | 8/2010 |
| JP | 2016-76566 A | 5/2016 |
| JP | 2016-86142 A | 5/2016 |
| JP | 2016-100364 A | 5/2016 |
| JP | 2017-218446 A | 12/2017 |
| KR | 10-2015-0102735 A | 9/2015 |
| KR | 10-2017-0100709 A | 9/2017 |
| KR | 10-2017-0126400 A | 11/2017 |
| KR | 10-2018-0116740 A | 10/2018 |
| KR | 10-2018-0131091 A | 12/2018 |
| KR | 10-2019-0003329 A | 1/2019 |
| WO | WO 2006/123667 A1 | 11/2006 |
| WO | WO 2016/009823 A1 | 1/2016 |
| WO | WO 2016/064111 A1 | 4/2016 |
| WO | WO 2017/135717 A1 | 8/2017 |
| WO | WO 2017/146406 A1 | 8/2017 |
| WO | WO 2019/135665 A1 | 7/2019 |
| WO | WO 2019/146946 A1 | 8/2019 |

OTHER PUBLICATIONS

Endo et al., "Efficient up-conversion of triplet excitons into a singlet state and its application for organic light emitting diodes", Applied Physics Letters, 98, 083302 (2011), total of 3 pages.
Hosokawa et al., "Development of Styryl-Based Light Emitting Material", Proceedings of the 9th Meeting of the Japan Society of Applied Physics, pp. 55-61 (2001).
International Search Report for PCT/JP2019/024590 (PCT/ISA/210) dated Sep. 24, 2019.
Wakimoto, "Optimization of driving lifetime durability in organic LED devices using phosphorescent guest emitter", Proceedings of the 9th Meeting of the Japan Society of Applied Physics, pp. 23-31 (2001).

* cited by examiner

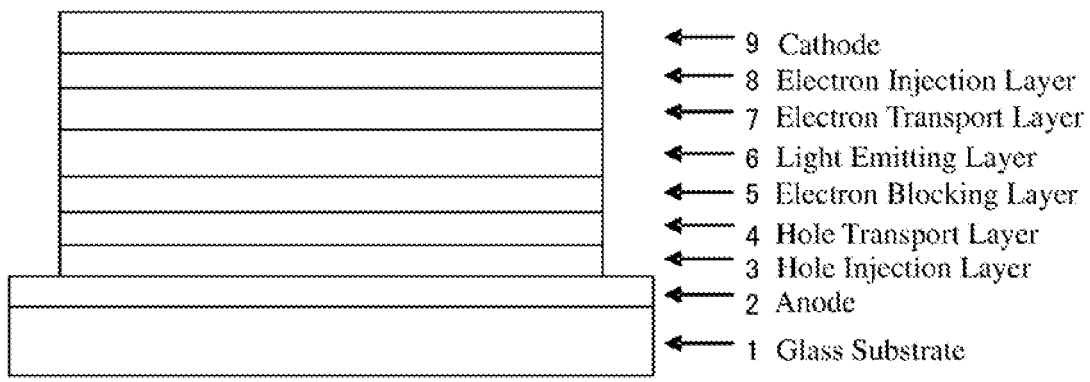

ic EL devices is based on Tg.
COMPOUND HAVING TRIARYLAMINE STRUCTURE AND ORGANIC ELECTROLUMINESCENCE DEVICE

TECHNICAL FIELD

The present invention relates to a compound that is suitable for organic electroluminescence devices (hereinafter referred to simply as "organic EL devices"), which are self-light-emitting devices favorably used in various display apparatuses, and more particularly relates to a compound having a triarylamine structure and an organic EL device in which the compound is used.

BACKGROUND ART

Since organic EL devices are self-emissive devices, they are brighter than liquid crystal devices, have superior display viewability, and can provide a clearer display. For these reasons, active studies have been carried out on organic EL devices.

In 1987, C. W. Tang et al. of Eastman Kodak Company made a practical organic EL device in which an organic material was used, by developing a device having a stacked layer structure in which various functions were assigned to different materials. They achieved a high luminance of 1,000 cd/m$^2$ or higher at a voltage of 10 V or less by stacking a layer of a fluorescent body capable of transporting electrons and a layer of an organic substance capable of transporting holes, injecting both charges into the fluorescent body layer, and thereby causing the layer to emit light (see Patent Literatures 1 and 2, for example).

Many improvements have been heretofore made to organic EL devices to put them to practical use. High efficiency and durability have been achieved by subdividing the functions assigned to respective layers of the stacked layer structure and forming an electroluminescence device in which an anode, a hole injection layer, a hole transport layer, a light emitting layer, an electron transport layer, an electron injection layer, and a cathode are sequentially provided on a substrate (see Non-Patent Literature 1, for example).

To further increase light emission efficiency, attempts have been made to utilize triplet excitons, and the utilization of phosphorescent light emitting compounds has been investigated (see Non-Patent Literature 2, for example).

Moreover, devices that utilize light emission based on thermally activated delayed fluorescence (TADF) have also been developed. In 2011, Adachi et al. from Kyushu University realized an external quantum efficiency of 5.3% with a device that uses a thermally activated delayed fluorescence material (see Non-Patent Literature 3, for example).

The light emitting layer can also be prepared by doping a charge transporting compound, generally called a host material, with a fluorescent compound, a phosphorescent light emitting compound, or a material that radiates delayed fluorescence. As stated in the non-patent literature above, the selection of the organic materials in an organic EL device greatly affects the characteristics of that device, such as efficiency and durability (see Non-Patent Literature 2, for example).

In an organic EL device, the charges injected from both electrodes recombine in the light emitting layer, thereby producing light emission, and how efficiently the charges of both the holes and the electrons are passed on to the light emitting layer is of importance. Therefore, a device that exhibits excellent carrier balance is required. Also, by improving electron blockability, that is, the ability to block electrons injected from the cathode, the probability of holes and electrons recombining is increased, and even higher light emission efficiency can be achieved. Therefore, the functions to be fulfilled by the hole transport material are important, and a hole transport material having high hole injectability, high hole mobility, high electron blockability, and high durability against electrons has been in demand.

Moreover, with regard to device lifespan, heat resistance and amorphousness of the materials are also important. A material with low heat resistance thermally decomposes due to heat produced during device driving, even at low temperatures, and the material deteriorates. A material with low amorphousness causes crystallization of a thin film to occur even in a short period of time, and the device deteriorates. Thus, high heat resistance and good amorphousness are required of the materials to be used.

N,N'-diphenyl-N,N'-di(α-naphthyl)benzidine (hereinafter abbreviated as NPD) and various aromatic amine derivatives are known as hole transport materials that have been heretofore used in organic EL devices (see Patent Literatures 1 and 2, for example). NPD has good hole transport capability, but the glass transition point (Tg), which is an indicator of heat resistance, is as low as 96° C., and therefore, under high-temperature conditions, the device characteristics degrade due to crystallization.

Moreover, among the aromatic amine derivatives disclosed in Patent Literatures 1 and 2, there are also compounds with an excellent hole mobility of 10$^{-3}$ cm$^2$/Vs or higher, but the electron blockability of these compounds is insufficient, which allows some electrons to pass through the light emitting layer, and therefore, there are problems in that, for example, no increase in light emission efficiency can be expected. Thus, materials with which thin films having higher electron blockability, higher stability, and higher heat resistance can be obtained are needed to further increase efficiency.

Furthermore, aromatic amine derivatives with high durability have also been reported (see Patent Literature 3, for example). However, these aromatic amine derivatives are used as charge transport materials in electrophotographic photoreceptors, and there are no examples of application to an organic EL device.

Arylamine compounds having a substituted carbazole structure have been suggested as compounds with improved properties such as heat resistance and hole injectability (see Patent Literatures 4 and 5, for example). However, even though heat resistance, light emission efficiency, and the like of devices in which these compounds are used for a hole injection layer or a hole transport layer have been improved, the results are still insufficient. Therefore, for a further decrease in driving voltage and a further increase in light emission efficiency, there is demand for a hole transport material having high hole injectability, high hole mobility, high electron blockability, and, furthermore, high durability against electrons.

CITATION LIST

Patent Literature

Patent Literature 1: U.S. Pat. No. 5,792,557
Patent Literature 2: U.S. Pat. No. 5,639,914
Patent Literature 3: U.S. Pat. No. 7,799,492
Patent Literature 4: U.S. Pat. No. 8,021,764
Patent Literature 5: EP 2684932

Non-Patent Literature

Non-Patent Literature 1: Proceedings of the 9th Meeting of the Japan Society of Applied Physics, pp. 55-61 (2001)
Non-Patent Literature 2: Proceedings of the 9th Meeting of the Japan Society of Applied Physics, pp. 23-31 (2001)
Non-Patent Literature 3: Appl. Phys. Let., 98, 083302 (2011)

SUMMARY OF INVENTION

An object of the present invention is to provide an organic compound that has excellent properties, with excellent hole injection and transport performance, electron blocking capability, and high stability in a thin film state, as a material for a highly efficient and highly durable organic EL device, and furthermore to provide a highly efficient and highly durable organic EL device by using this compound.

An organic compound to be provided by the present invention should have the following physical properties: (1) good hole injection properties, (2) high hole mobility, (3) excellent electron blocking capability, (4) stability in a thin film state, and (5) excellent heat resistance.

Moreover, an organic EL device to be provided by the present invention should have the following physical characteristics: (1) high light emission efficiency and high power efficiency, (2) a low light-emission start voltage, (3) a low actual driving voltage, and (4) a long lifespan.

To achieve the above-described object, the inventors of the present invention conducted in-depth research, and found that a triarylamine compound having a specific structure has excellent hole injection and transport capabilities, as well as excellent stability and durability of a thin film, and furthermore, also has excellent electron blockability. Thus, the present invention was accomplished.

That is, the present invention provides the followings:

1) A compound having a triarylamine structure and being represented by the structural formula (A-1) below:

[Chem. 1]

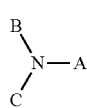

(A-1)

where A, B, and C may be the same or different, and each represent a group represented by the structural formula (B-1) below, a substituted or unsubstituted aromatic hydrocarbon group, a substituted or unsubstituted aromatic heterocyclic group, or a substituted or unsubstituted fused polycyclic aromatic group, where at least one of A, B, and C is not the group represented by the structural formula (B-1) below:

[Chem. 2]

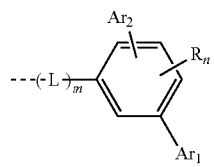

(B-1)

where the dashed line portion represents a binding site;

R represents a hydrogen atom, a heavy hydrogen atom, a fluorine atom, a chlorine atom, a cyano group, a nitro group, a linear or branched alkyl group having 1 to 6 carbon atoms and optionally having a substituent, a cycloalkyl group having 5 to 10 carbon atoms and optionally having a substituent, a linear or branched alkenyl group having 2 to 6 carbon atoms and optionally having a substituent, a linear or branched alkyloxy group having 1 to 6 carbon atoms and optionally having a substituent, a cycloalkyloxy group having 5 to 10 carbon atoms and optionally having a substituent, a substituted or unsubstituted aromatic heterocyclic group, a substituted or unsubstituted aromatic hydrocarbon group, a substituted or unsubstituted fused polycyclic aromatic group, or a substituted or unsubstituted aryloxy group; n is the number of Rs and represents an integer of 0 to 3, where, when n is 2 or 3, the plurality of Rs bonded to the same benzene ring may be the same or different and may be bonded to each other to form a ring via a single bond, a substituted or unsubstituted methylene group, an oxygen atom, or a sulfur atom;

L represents a substituted or unsubstituted aromatic hydrocarbon group, a substituted or unsubstituted aromatic heterocyclic group, or a substituted or unsubstituted fused polycyclic aromatic group; m represents an integer of 1 to 3, where, when m is 2 or 3, Ls may be the same or different; and $Ar_1$ and $Ar_2$ may be the same or different, and each represent a substituted or unsubstituted aromatic hydrocarbon group, a substituted or unsubstituted aromatic heterocyclic group, or a substituted or unsubstituted fused polycyclic aromatic group.

2) The compound having a triarylamine structure as set forth in clause 1) above, wherein the group represented by the structural formula (B-1) is a group represented by the structural formula (B-2) below:

[Chem. 3]

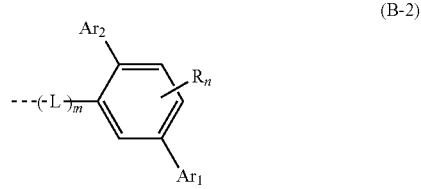

(B-2)

where $Ar_1$, $Ar_2$, L, m, n, and R are as defined in the structural formula (B-1).

3) The compound having a triarylamine structure as set forth in clause 2) above, wherein L in the group represented by the structural formula (B-2) is an unsubstituted aromatic hydrocarbon group, an unsubstituted aromatic heterocyclic group, or an unsubstituted fused polycyclic aromatic group.

4) The compound having a triarylamine structure as set forth in clause 3) above, wherein the group represented by the structural formula (B-2) is a group represented by the structural formula (B-3) below:

[Chem. 4]

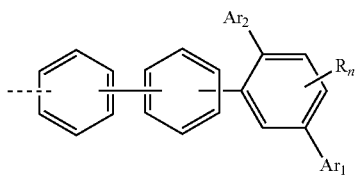

(B-3)

where Ar$_1$, Ar$_2$, n, and R are as defined in the structural formula (B-1).

5) The compound having a triarylamine structure as set forth in clause 3) above, wherein the group represented by the structural formula (B-2) is a group represented by the structural formula (B-4) below:

[Chem. 5]

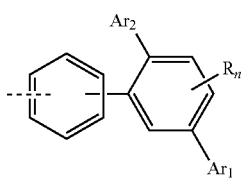

(B-4)

where Ar$_1$, Ar$_2$, n, and R are as defined in the structural formula (B-1).

6) The compound having a triarylamine structure as set forth in clause 5) above, wherein the group represented by the structural formula (B-4) is a group represented by the structural formula (B-5) below:

[Chem. 6]

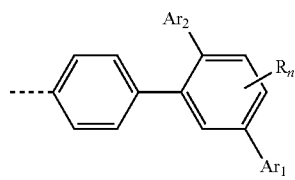

(B-5)

where Ar$_1$, Ar$_2$, n, and R are as defined in the structural formula (B-1).

7) The compound having a triarylamine structure as set forth in clause 6) above, wherein n in the structural formula (B-5) is 0 or 1.

8) The compound having a triarylamine structure as set forth in clause 6) above, wherein n in the structural formula (B-5) is 0.

9) The compound having a triarylamine structure as set forth in clause 4) above, wherein the group represented by the structural formula (B-3) is a group represented by the structural formula (B-6) below:

[Chem. 6]

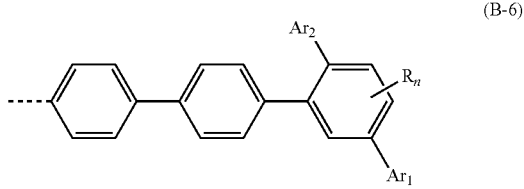

(B-6)

where Ar$_1$, Ar$_2$, n, and R are as defined in the (B-1).

10) The compound having a triarylamine structure as set forth in clause 9) above, wherein n in the structural formula (B-6) is 0 or 1.

11) The compound having a triarylamine structure as set forth in clause 9) above, wherein n in the structural formula (B-6) is 0.

12) An organic EL device including a pair of electrodes and one or more organic layers sandwiched therebetween, wherein the compound having a triarylamine structure as set forth in any one of clauses 1) to 11) above is used as a constituent material of at least one of the organic layers.

13) The organic EL device as set forth in clause 12) above, wherein the at least one organic layer is a hole transport layer.

14) The organic EL device as set forth in clause 12) above, wherein the at least one organic layer is an electron blocking layer.

15) The organic EL device as set forth in clause 12) above, wherein the at least one organic layer is a hole injection layer.

16) The organic EL device as set forth in clause 12) above, wherein the at least one organic layer is a light emitting layer.

Specific examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by R in the structural formulae (B-1) to (B-6) include a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzooxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, a carbolinyl group, and the like. Furthermore, the group may also be selected from aryl groups having 6 to 30 carbon atoms and heteroaryl groups having 2 to 30 carbon atoms. These substituents and the benzene rings substituted by the substituents, as well as a plurality of substituents that substitute the same benzene ring may be bonded to each other to form a ring via a single bond, a substituted or unsubstituted methylene group, a substituted or unsubstituted amino group, an oxygen atom, or a sulfur atom.

Specific examples of the "linear or branched alkyl group having 1 to 6 carbon atoms", the "cycloalkyl group having 5 to 10 carbon atoms", or the "linear or branched alkenyl group having 2 to 6 carbon atoms" of the "linear or branched alkyl group having 1 to 6 carbon atoms and optionally having a substituent", the "cycloalkyl group having 5 to 10 carbon atoms and optionally having a substituent", or the "linear or branched alkenyl group having 2 to 6 carbon atoms and optionally having a substituent" represented by R in the structural formulae (B-1) to (B-6) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, a 2-butenyl group, and the like. These substituents and the benzene rings substituted by the substituents, as well as a plurality of substituents that substitute the same benzene ring may be bonded to each other to form a ring via a single bond, a substituted or unsubstituted methylene group, a substituted or unsubstituted amino group, an oxygen atom, or a sulfur atom.

Specific examples of the "linear or branched alkyloxy group having 1 to 6 carbon atoms" or the "cycloalkyloxy group having 5 to 10 carbon atoms" of the "linear or branched alkyloxy group having 1 to 6 carbon atoms and optionally having a substituent" or the "cycloalkyloxy group having 5 to 10 carbon atoms and optionally having a substituent" represented by R in the structural formulae (B-1) to (B-6) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, a 2-adamantyloxy group, and the like. These substituents and the benzene rings substituted by the substituents, as well as a plurality of substituents that substitute the same benzene ring may be bonded to each other to form a ring via a single bond, a substituted or unsubstituted methylene group, a substituted or unsubstituted amino group, an oxygen atom, or a sulfur atom.

Specific examples of the "substituent" of the "substituted aromatic hydrocarbon group", the "substituted aromatic heterocyclic group", the "substituted fused polycyclic aromatic group", the "linear or branched alkyl group having 1 to 6 carbon atoms and optionally having a substituent", the "cycloalkyl group having 5 to 10 carbon atoms and optionally having a substituent", the "linear or branched alkenyl group having 2 to 6 carbon atoms and optionally having a substituent", the "linear or branched alkyloxy group having 1 to 6 carbon atoms and optionally having a substituent", or the "cycloalkyloxy group having 5 to 10 carbon atoms and optionally having a substituent" represented by R in the structural formulae (B-1) to (B-6) include the following groups: a heavy hydrogen atom, a cyano group, and a nitro group; halogen atoms such as a fluorine atom, a chlorine atom, a bromine atom, and an iodine atom; silyl groups such as a trimethylsilyl group and a triphenylsilyl group; linear or branched alkyl groups having 1 to 6 carbon atoms such as a methyl group, an ethyl group, and a propyl group; linear or branched alkyloxy groups having 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or fused polycyclic aromatic groups such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; and aromatic heterocyclic groups such as a pyridyl group, a thienyl group, a furyl group, a pyrrolyl group, a quinolyl group, an isoquinolyl group, a benzofuranyl group, a benzothienyl group, an indolyl group, a carbazolyl group, a benzooxazolyl group, a benzothiazolyl group, a quinoxalinyl group, a benzimidazolyl group, a pyrazolyl group, a dibenzofuranyl group, a dibenzothienyl group, and a carbolinyl group. These substituents may further be substituted by any of the substituents listed above as examples. Moreover, these substituents and the benzene rings substituted by the substituents, as well as a plurality of substituents that substitute the same benzene ring may be bonded to each other to form a ring via a single bond, a substituted or unsubstituted methylene group, a substituted or unsubstituted amino group, an oxygen atom, or a sulfur atom.

Examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by $Ar_1$ and $Ar_2$ in the structural formulae (B-1) to (B-6) are similar to those listed above as examples with respect to the "aromatic hydrocarbon group", the "aromatic heterocyclic group", or the "fused polycyclic aromatic group" represented by R in the structural formulae (B-1) to (B-5). The same holds true for the forms that the group can take.

Examples of the "substituent" of the "substituted aromatic hydrocarbon group", the "substituted aromatic heterocyclic group", or the "substituted fused polycyclic aromatic group" represented by $Ar_1$ and $Ar_2$ in the structural formulae (B-1) to (B-6) are similar to those listed above as examples with respect to the "substituent" of those represented by R in the structural formulae (B-1) to (B-5). The same holds true for the forms that the substituent can take.

Examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by A, B, and C in the structural formula (A-1) are similar to those listed above as examples with respect to the "aromatic hydrocarbon group", the "aromatic heterocyclic group", or the "fused polycyclic aromatic group" represented by R in the structural formulae (B-1) to (B-6). The same holds true for the forms that the group can take.

Examples of the "substituent" of the "substituted aromatic hydrocarbon group", the "substituted aromatic heterocyclic group", or the "substituted fused polycyclic aromatic group" represented by A, B, and C in the structural formula (A-1) are similar to those listed above as examples with respect to the "substituent" of those represented by R in the structural formulae (B-1) to (B-6). The same holds true for the forms that the substituent can take.

Examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by L in the structural formulae (B-1) to (B-6) are similar to those listed above as examples with respect to the "aromatic hydrocarbon group", the "aromatic heterocyclic group", or the "fused polycyclic aromatic group" represented by R in the structural formulae (B-1) to (B-6). The same holds true for the forms that the group can take.

Examples of the "substituent" of the "substituted aromatic hydrocarbon group", the "substituted aromatic heterocyclic group", or the "substituted fused polycyclic aromatic group" represented by L in the structural formulae (B-1) to (B-6) are similar to those listed above as examples with respect to the "substituent" of those represented by R in the structural formulae (B-1) to (B-6). The same holds true for the forms that the substituent can take.

In the present invention, it is preferable that A in the structural formula (A-1) is a group represented by the structural formula (B-1). In this case, B and C may be the same or different, and are each preferably a group represented by the structural formula (C-1) or (C-2) below.

[Chem. 8]

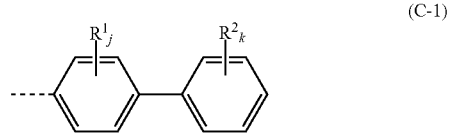

(C-1)

In the structural formula (C-1), $R^1$ and $R^2$ may be the same or different, and each represent a linear or branched alkyl group having 1 to 6 carbon atoms; j is the number of $R^1$s and represents an integer of 0 to 2; and k is the number of $R^2$s and represents an integer of 0 to 2, where j+k is 0 or 2, and when j+k is 2, $R^1$s, $R^2$s, or $R^1$ and $R^2$ are located adjacent to each other and bonded to each other to form a ring.

[Chem. 9]

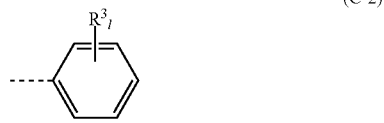

(C-2)

In the structural formula (C-2), les may be the same or different, and each represent a linear or branched alkyl group having 1 to 6 carbon atoms; and l is the number of $R^3$s and represents 0, 2, or 4, where, when l is 2 or 4, $R^3$s are located adjacent to each other and bonded to each other to form a ring.

The compound having a triarylamine structure and being represented by the structural formula (A-1) and being suitable for use in an organic EL device of the present invention can be used as the materials of a hole injection layer, a hole transport layer, and an electron blocking layer of the organic EL device. In particular, having the high hole mobility, this compound is preferable as the materials of a hole injection layer and a hole transport layer.

The organic EL device of the present invention uses the material for organic EL devices that has excellent hole injection and transport performance, and excellent electron blocking performance, as well as excellent stability and durability of a thin film. Therefore, the organic EL device of the present invention has higher hole transport efficiency of transporting holes from the hole transport layer to the light emitting layer than conventional organic EL devices, and, accordingly, has higher light emission efficiency and a lower driving voltage, and hence higher durability. The use of the compound having a triarylamine structure and being represented by the structural formula (A-1) makes it possible to realize an organic EL device having high efficiency, a low driving voltage, and a long lifespan.

Advantageous Effects of Invention

With an organic EL device of the present invention, since a compound having a specific triarylamine structure and being capable of effectively performing the hole injection and transport functions is selected, holes can be efficiently injected and transported from the hole transport layer to the light emitting layer, and therefore, it is possible to realize an organic EL device having excellent hole injection and transport performance, excellent stability and durability of a thin film, high efficiency, a low driving voltage, and a long lifespan.

According to the present invention, it is possible to improve the light emission efficiency, the driving voltage, and the durability of an organic EL device.

BRIEF DESCRIPTION OF DRAWINGS

FIG. 1 is a schematic diagram showing the configuration of an organic EL device of the present invention.

DESCRIPTION OF EMBODIMENTS

Specific examples of preferred compounds, of compounds having a triarylamine structure and being represented by the structural formula (A-1) and being suitable for use in an organic EL device of the present invention, will be given below. However, the present invention is not limited to these compounds.

[Chem. 10]

(Compound-1)

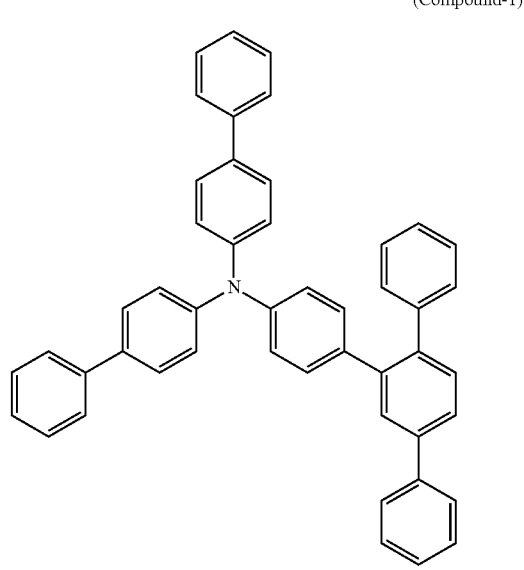

(Compound-2)
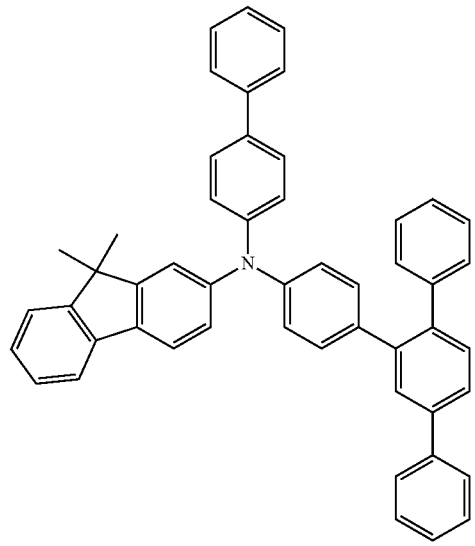
(Compound-3)
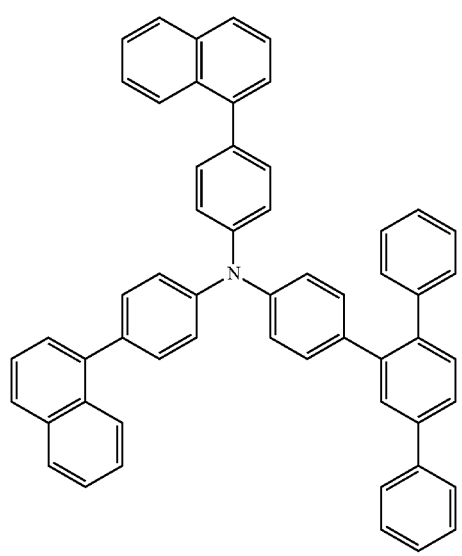
(Compound-4)
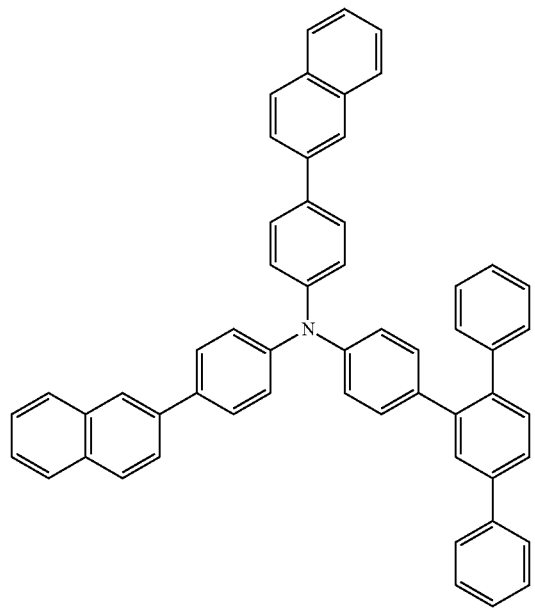
(Compound-5)
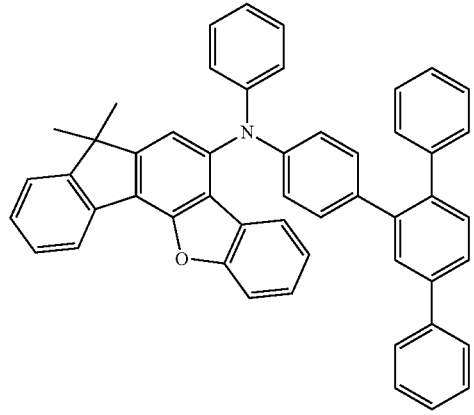
(Compound-6)
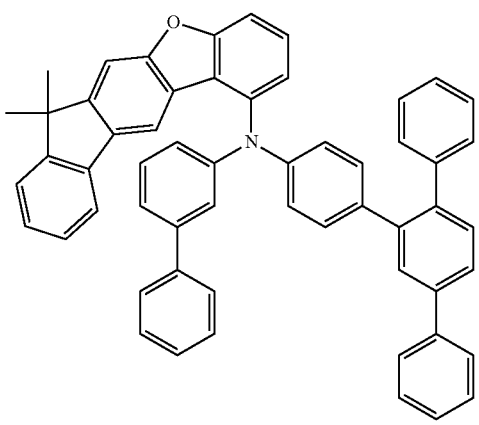

(Compound-7)
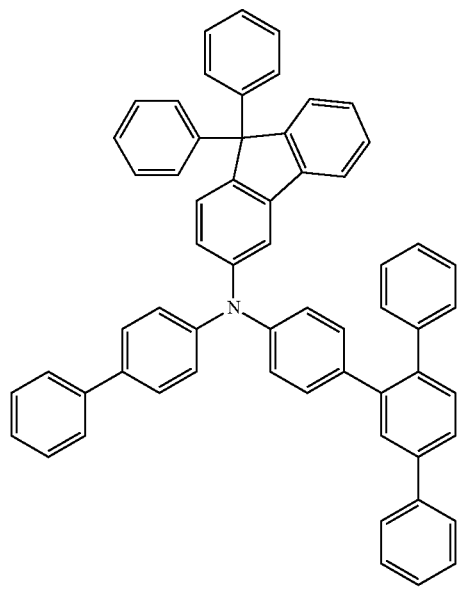
(Compound-8)
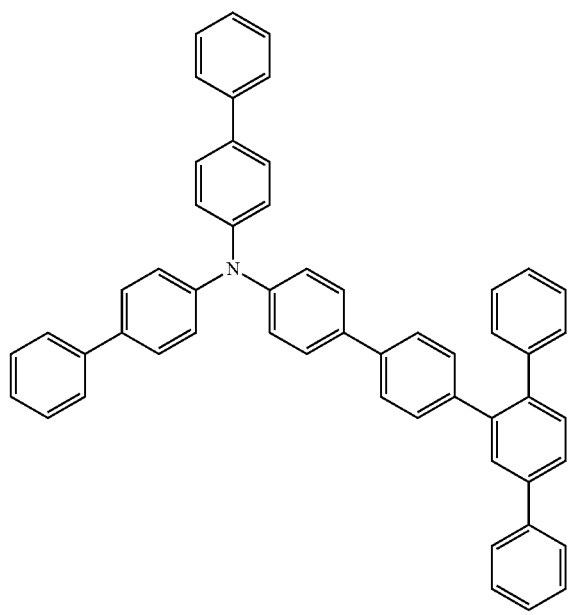
(Compound-9)
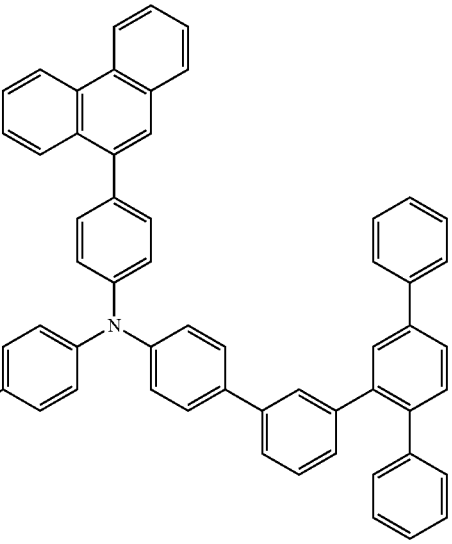
(Compound-10)

[Chem. 11]
(Compound-11)
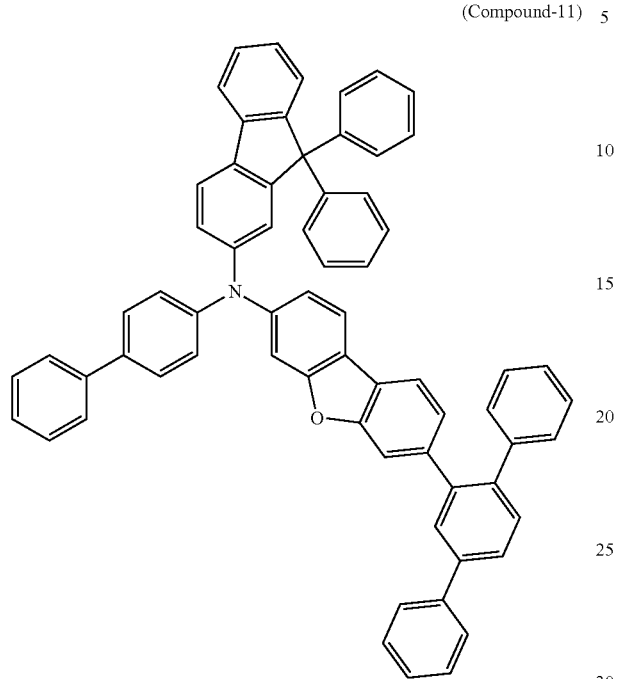
(Compound-13)
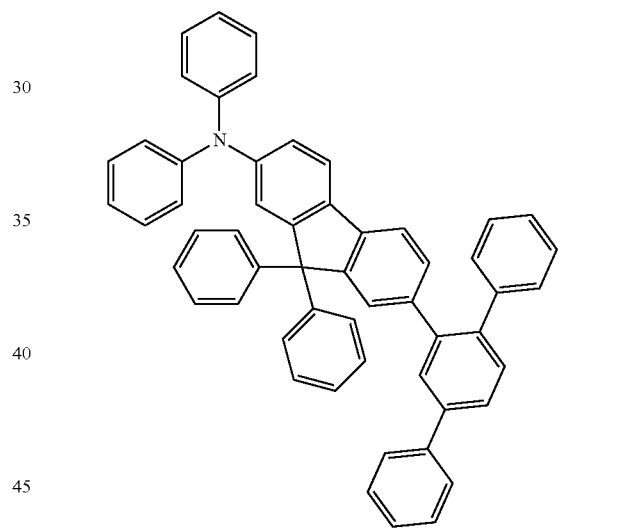
(Compound-14)
(Compound-12)
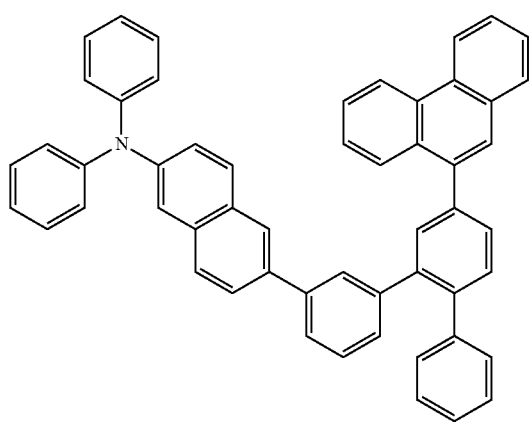
(Compound-15)
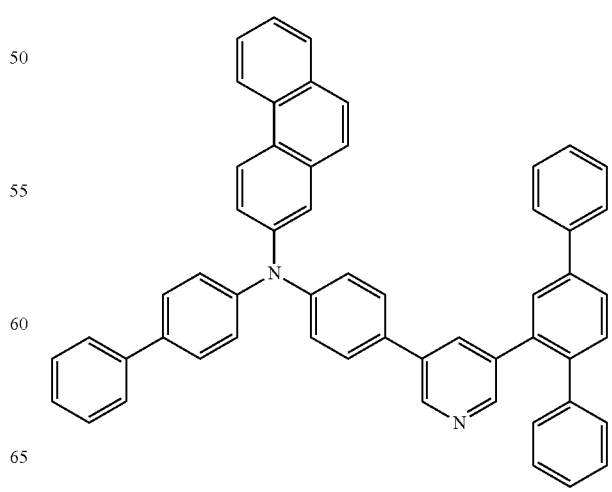

(Compound-16)
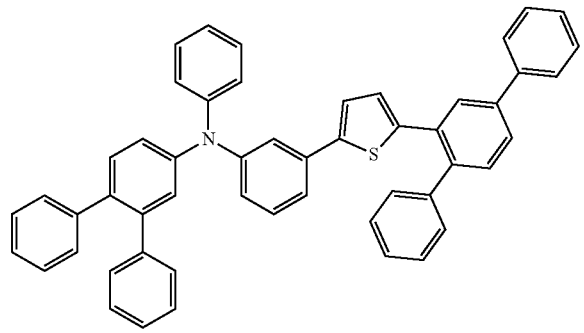
(Compound-17)
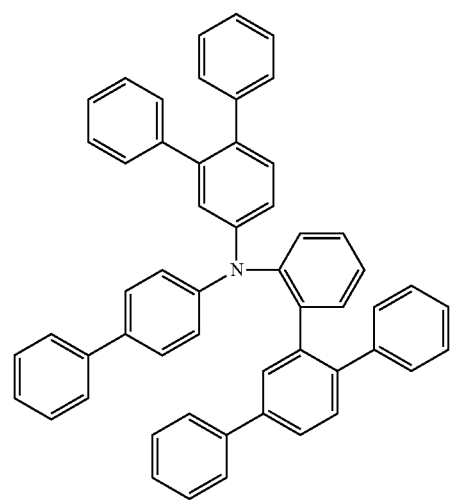
(Compound-18)
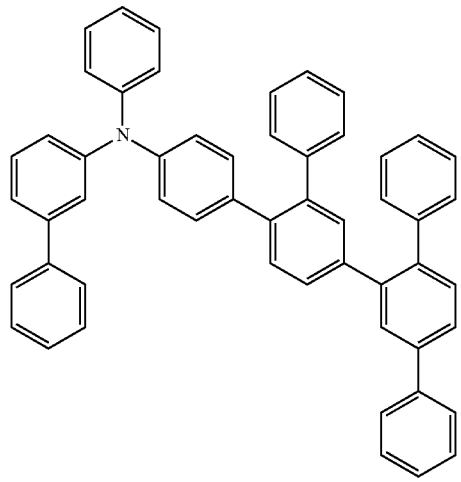
(Compound-19)
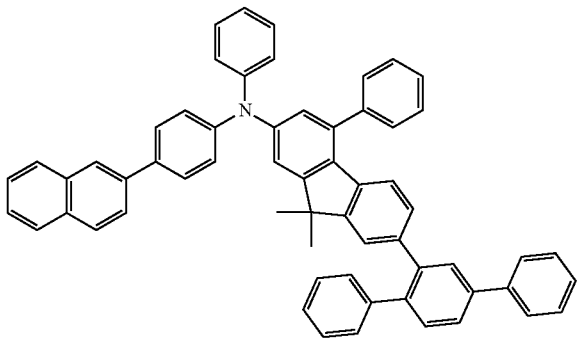
(Compound-20)
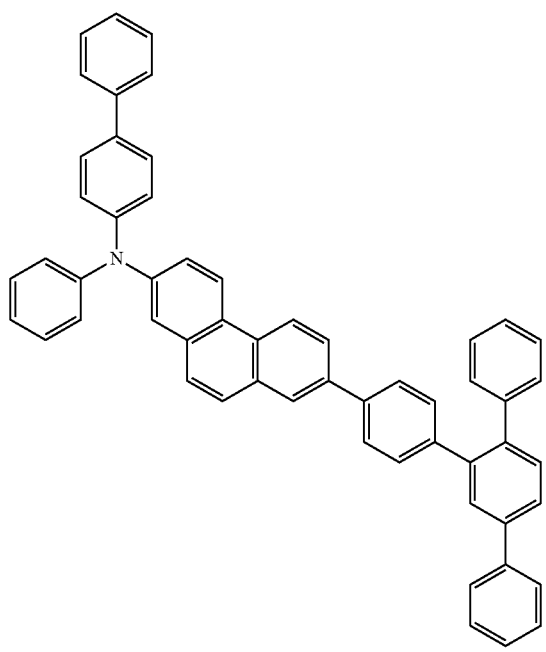
(Compound-21)

(Compound-22)
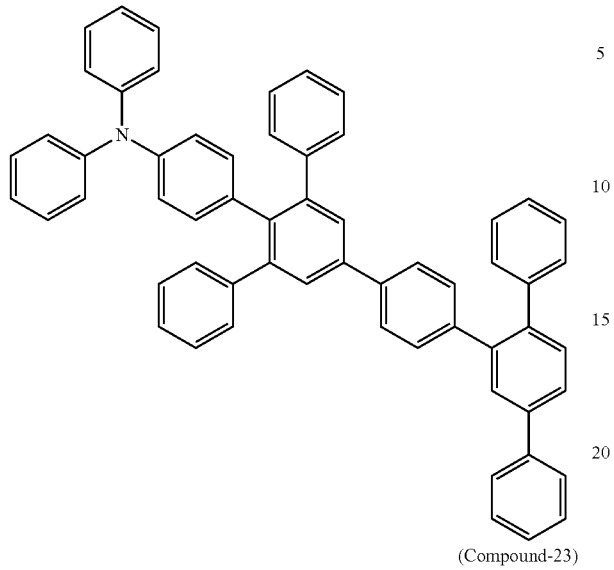
(Compound-23)
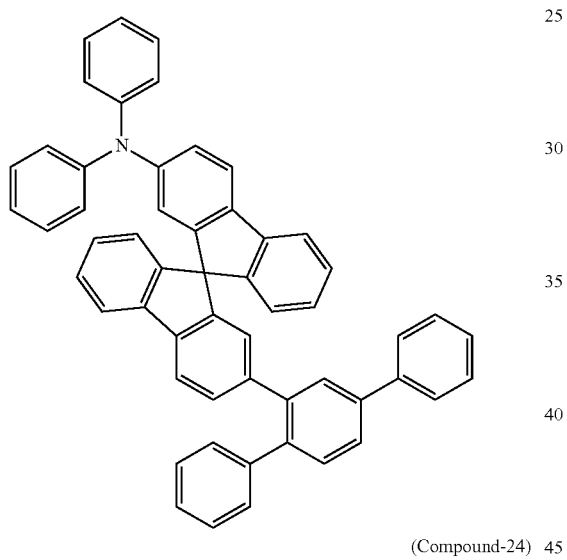
(Compound-24)
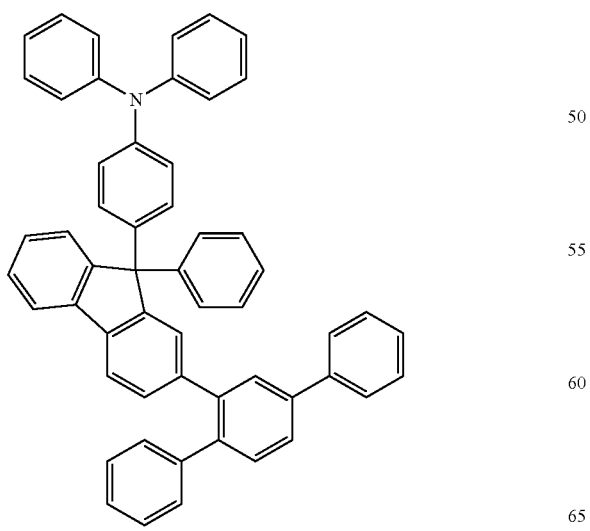
(Compound-25)
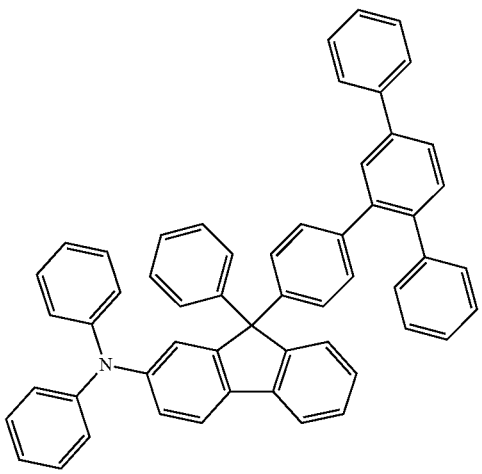
(Compound-26)
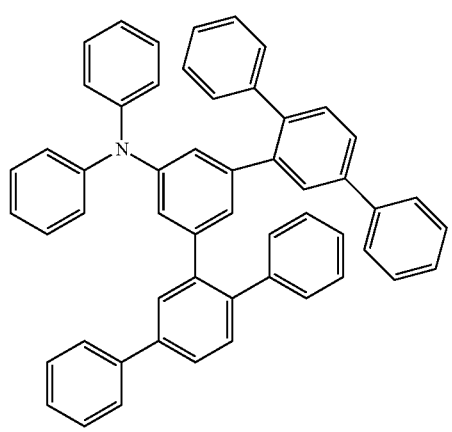
(Compound-27)
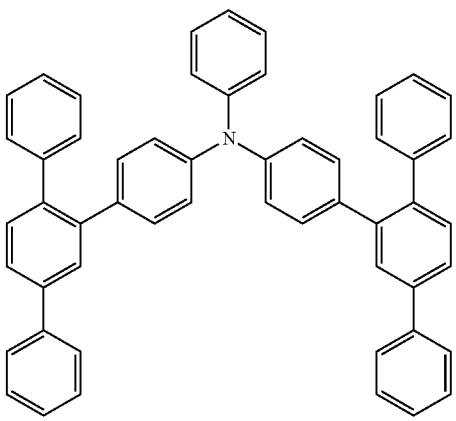

(Compound-28)
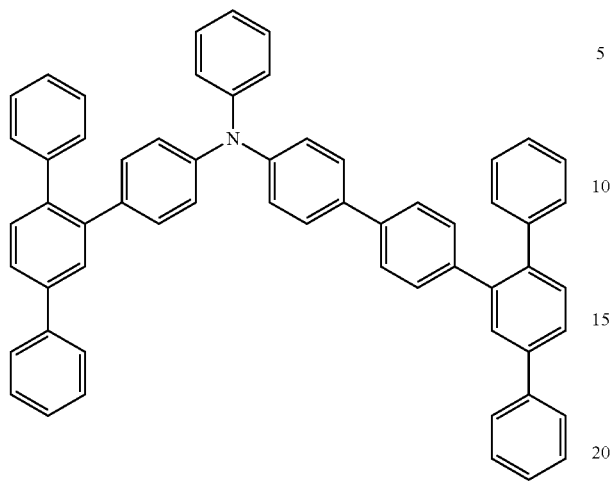
(Compound-31)
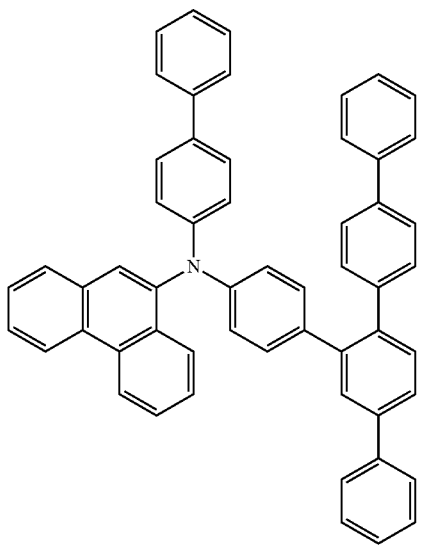
(Compound-29)
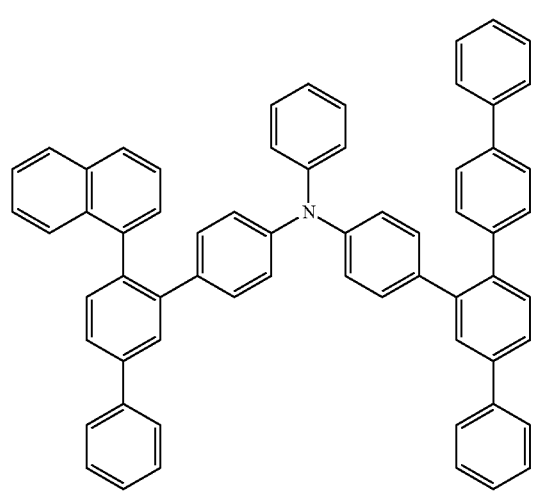
(Compound-32)
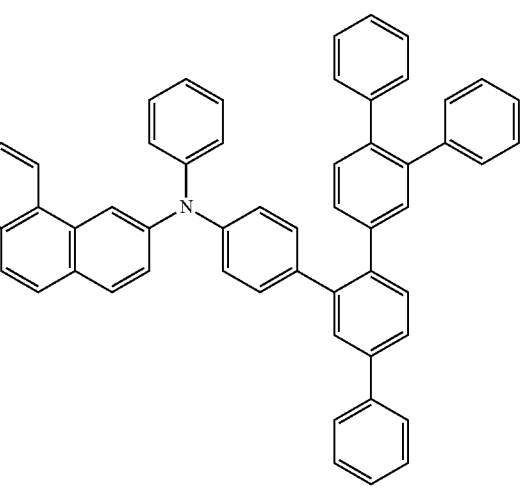
(Compound-30)
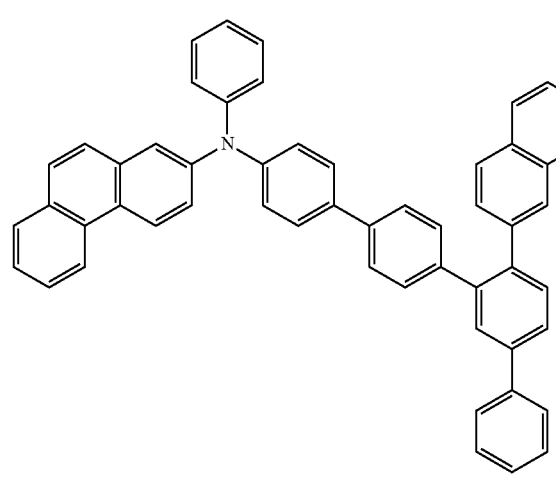
(Compound-33)
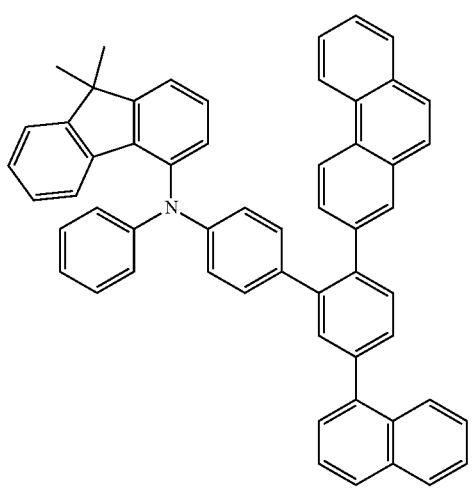

(Compound-34)
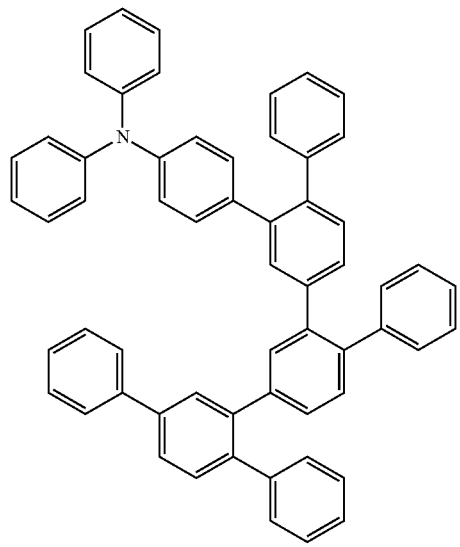
(Compound-35)
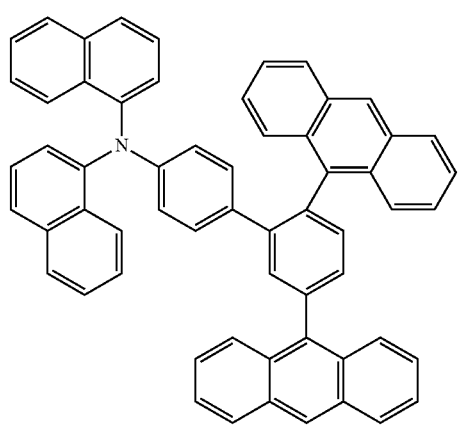
(Compound-36)
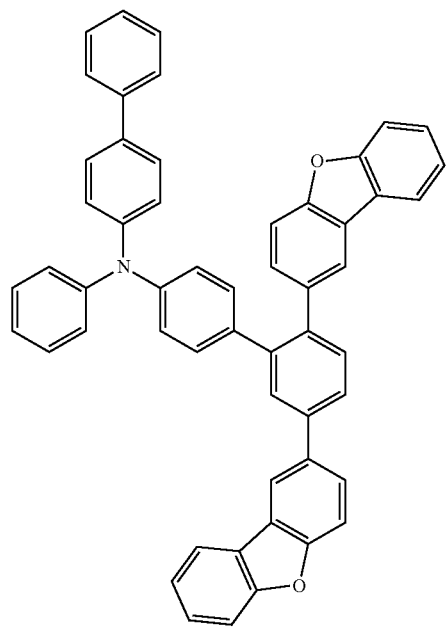
[Chem. 13]
(Compound-37)
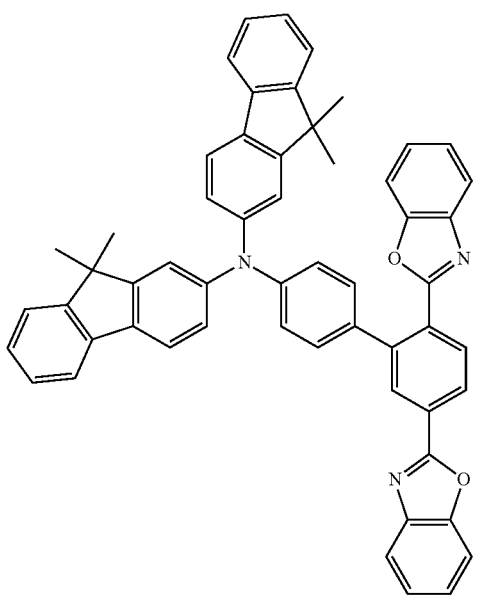
(Compound-38)
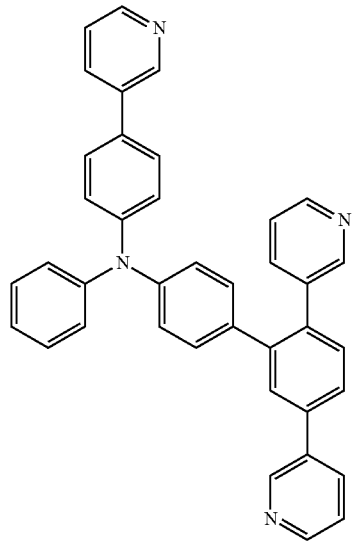

(Compound-39)
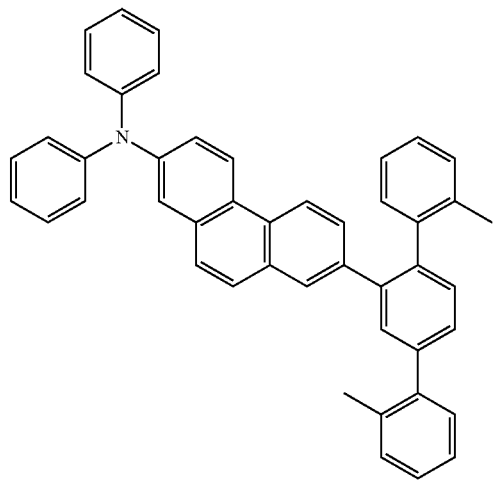
(Compound-40)
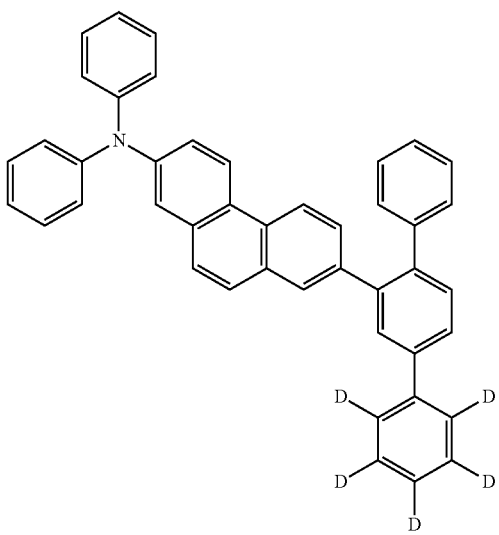
(Compound-41)
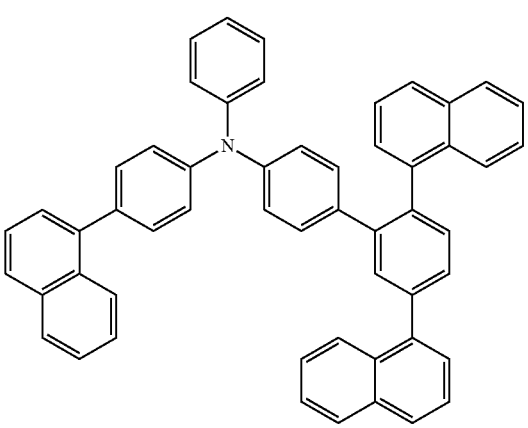
(Compound-42)
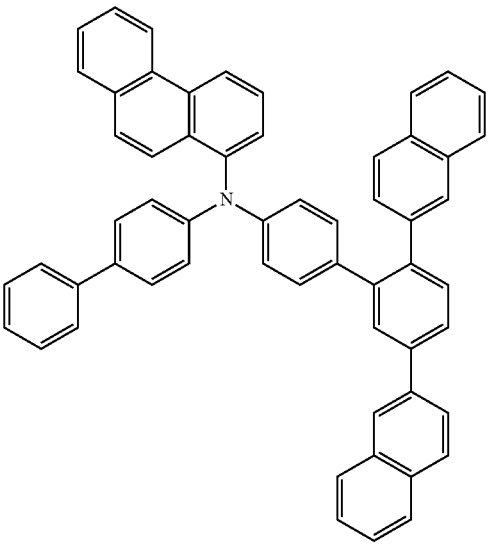
(Compound-43)
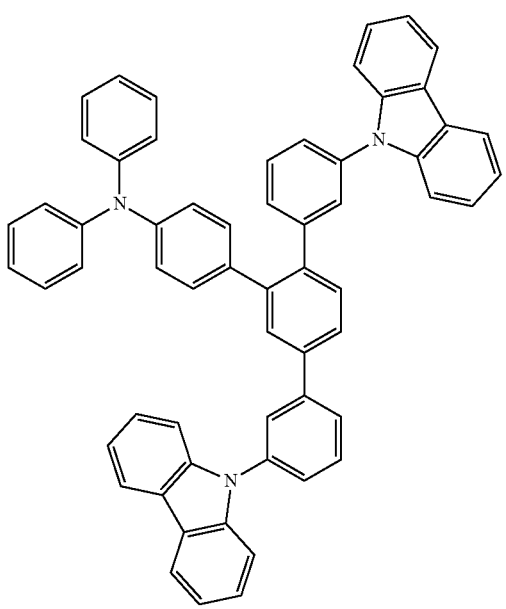

(Compound-44)
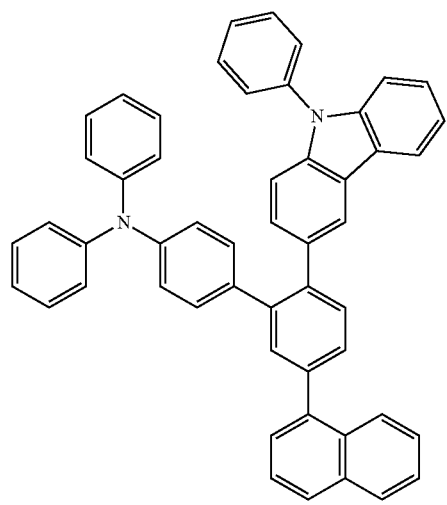
(Compound-45)
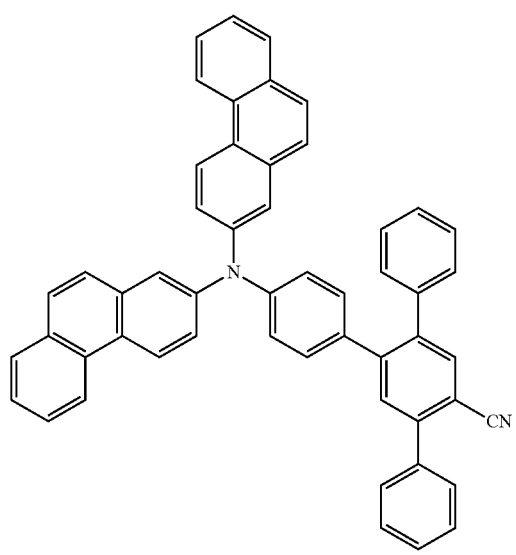
(Compound-46)
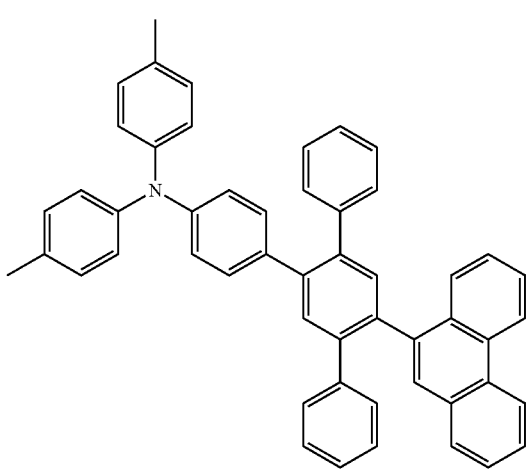
(Compound-47)
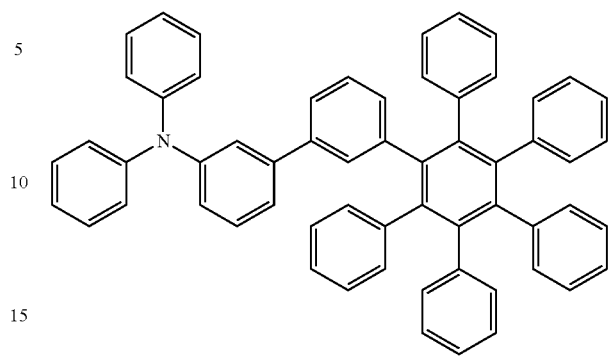
(Compound-48)
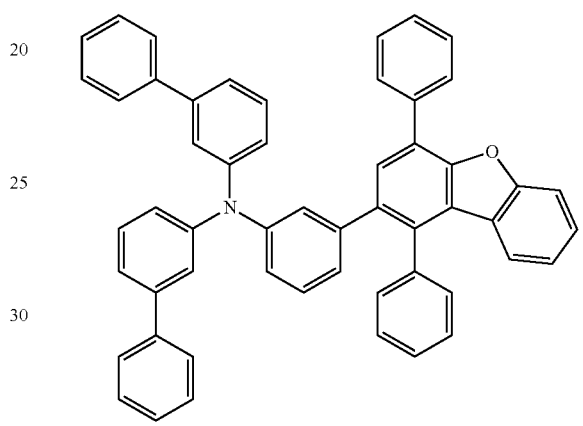
[Chem. 14]
(Compound-49)
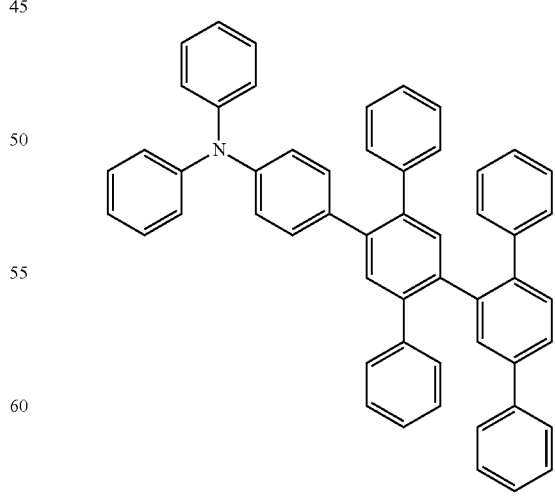

(Compound-50)
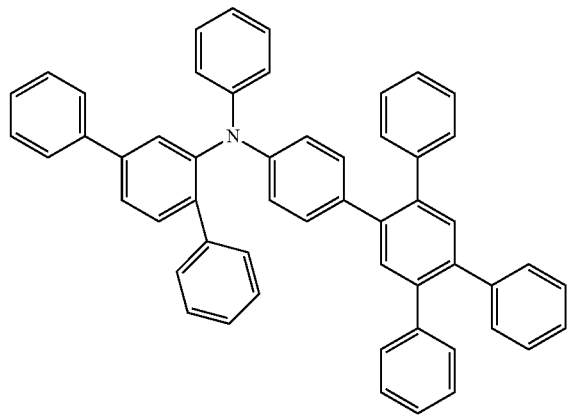
(Compound-51)
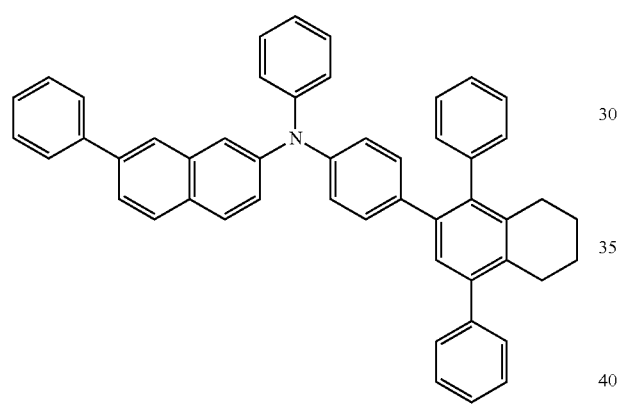
(Compound-52)
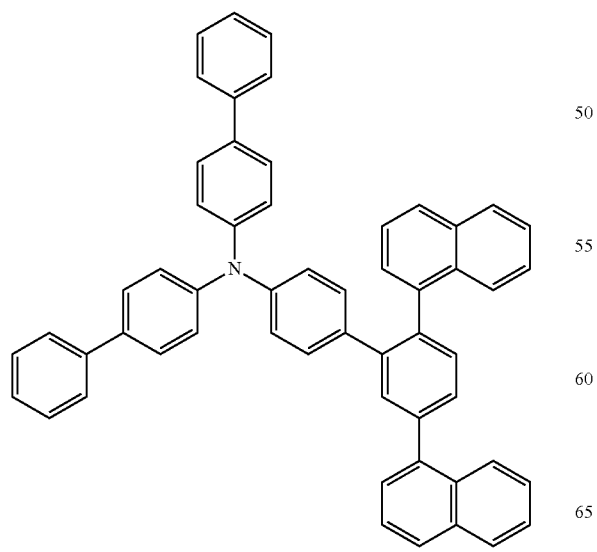
(Compound-53)
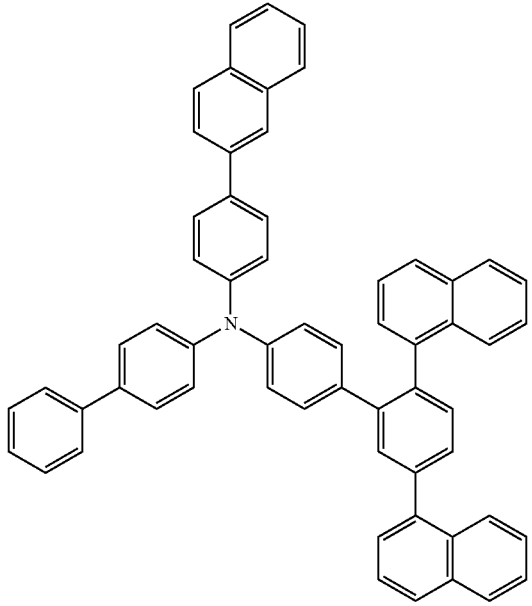
(Compound-54)
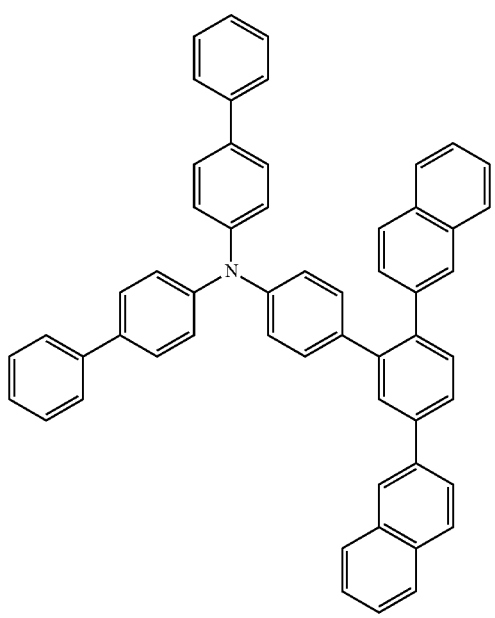

(Compound-55)
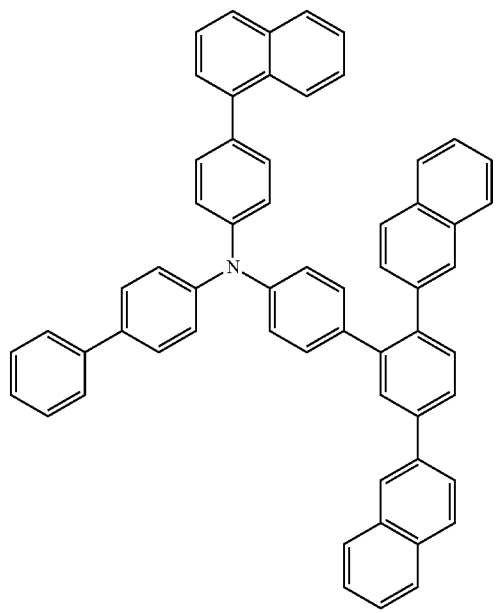
(Compound-56)
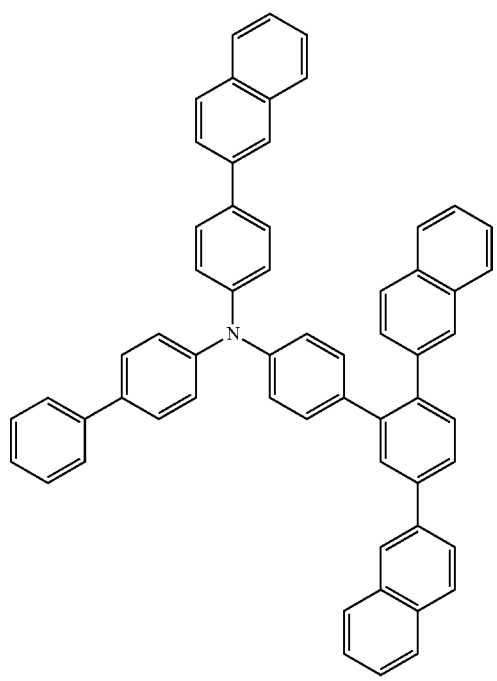
(Compound-57)
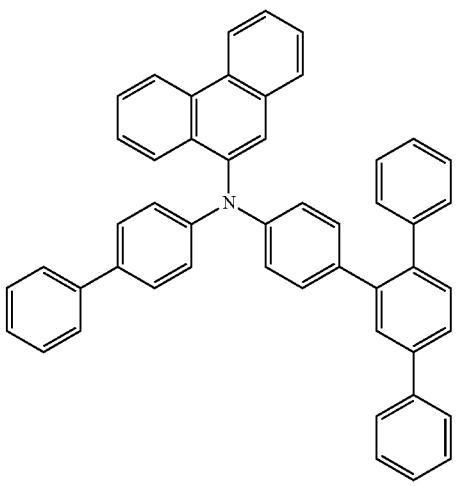
(Compound-58)
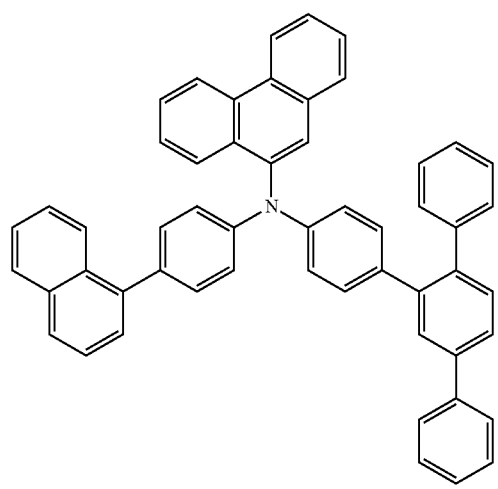
(Compound-59)
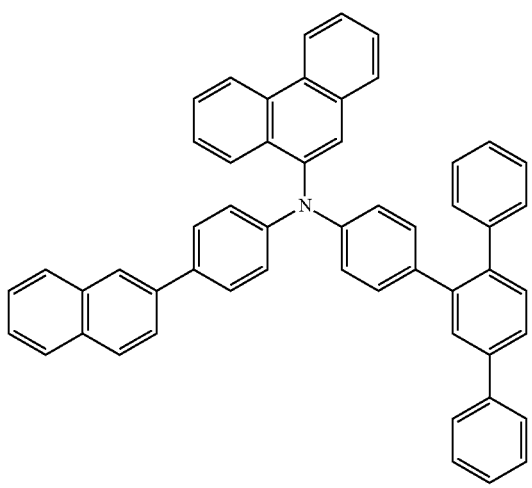

(Compound-60)
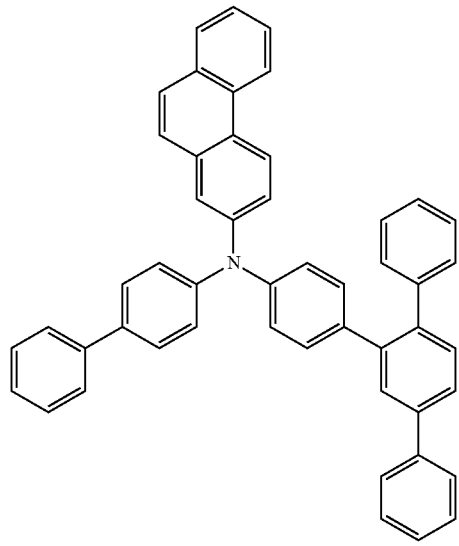
(Compound-62)
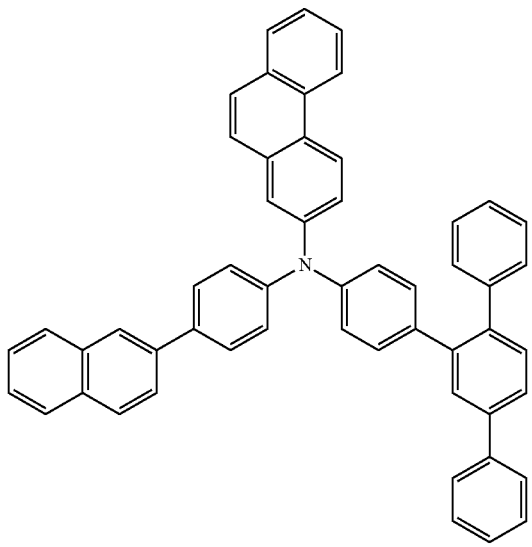
[Chem. 15]
(Compound-61)
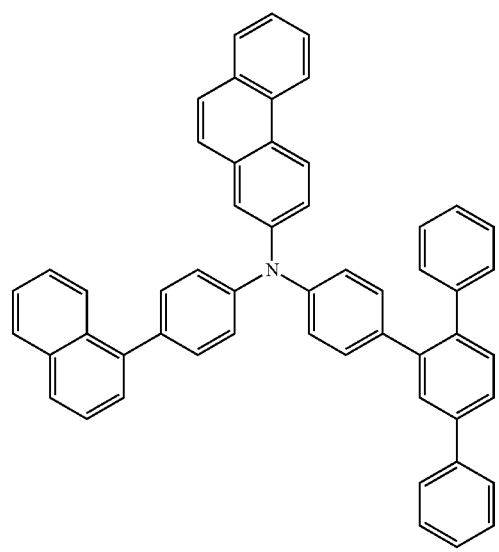
(Compound-63)
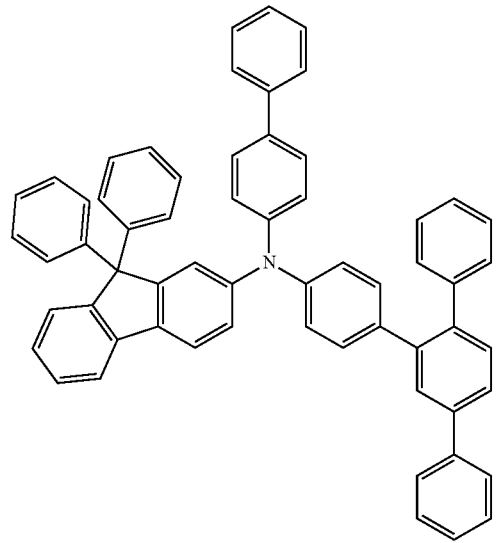

(Compound-64)
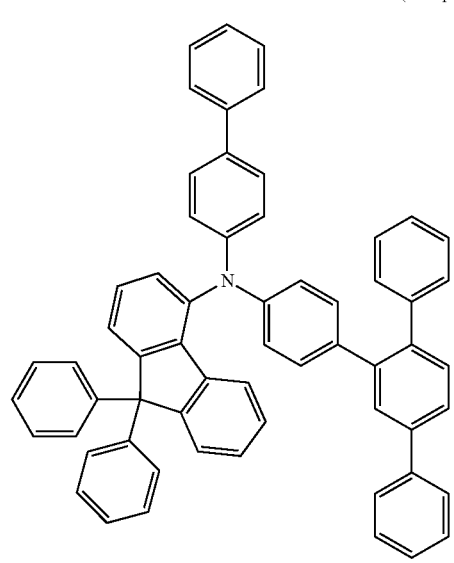
(Compound-65)
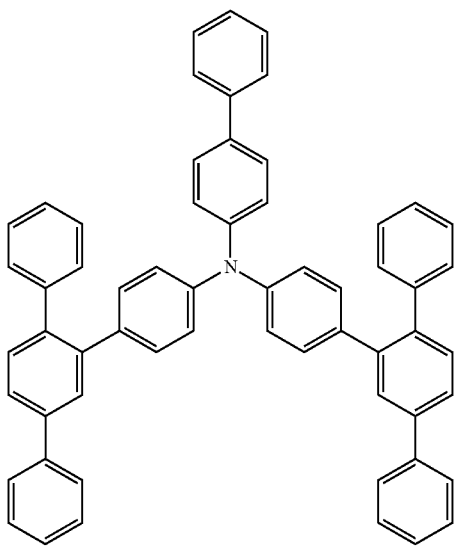
(Compound-66)
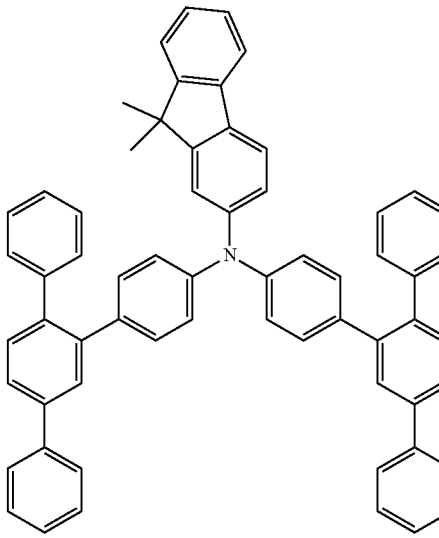
(Compound-67)
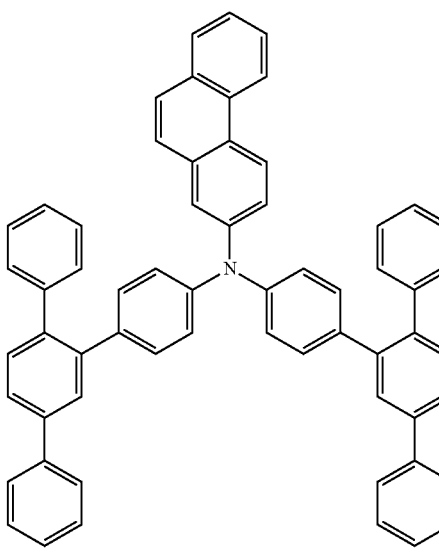
(Compound-68)
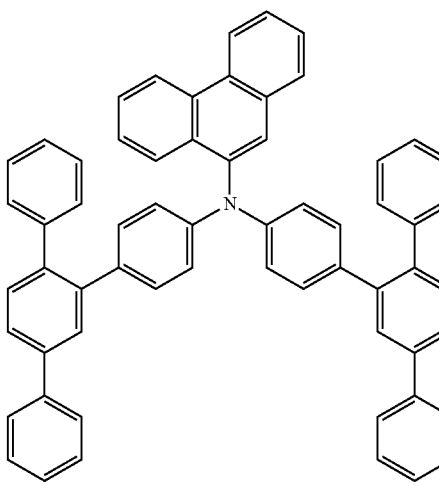

(Compound-69)
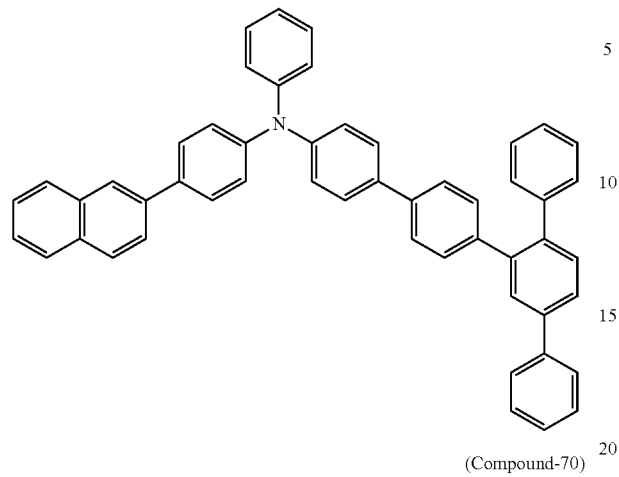
(Compound-70)
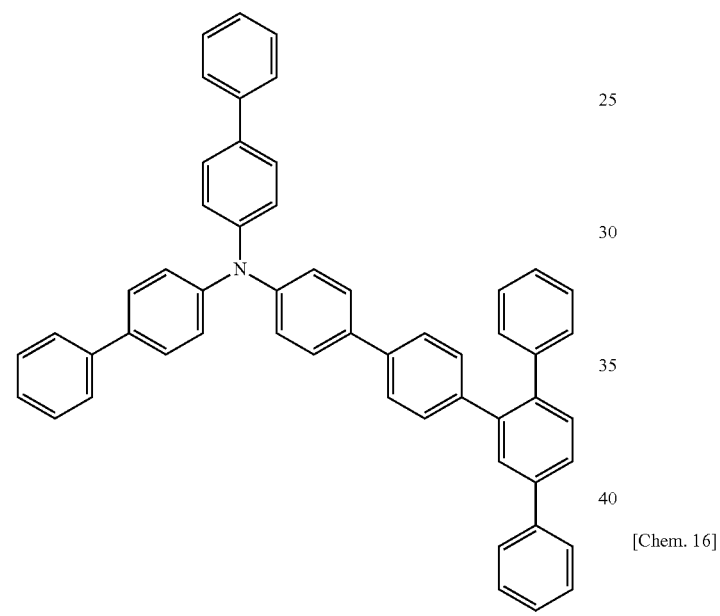
(Compound-71)
(Compound-72)
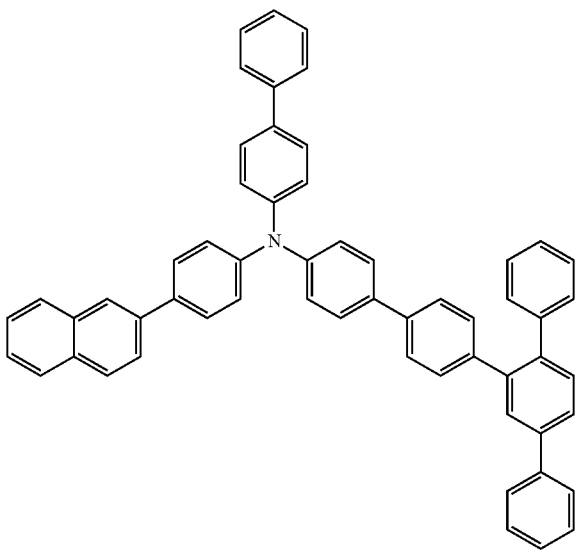
[Chem. 16]
(Compound-73)
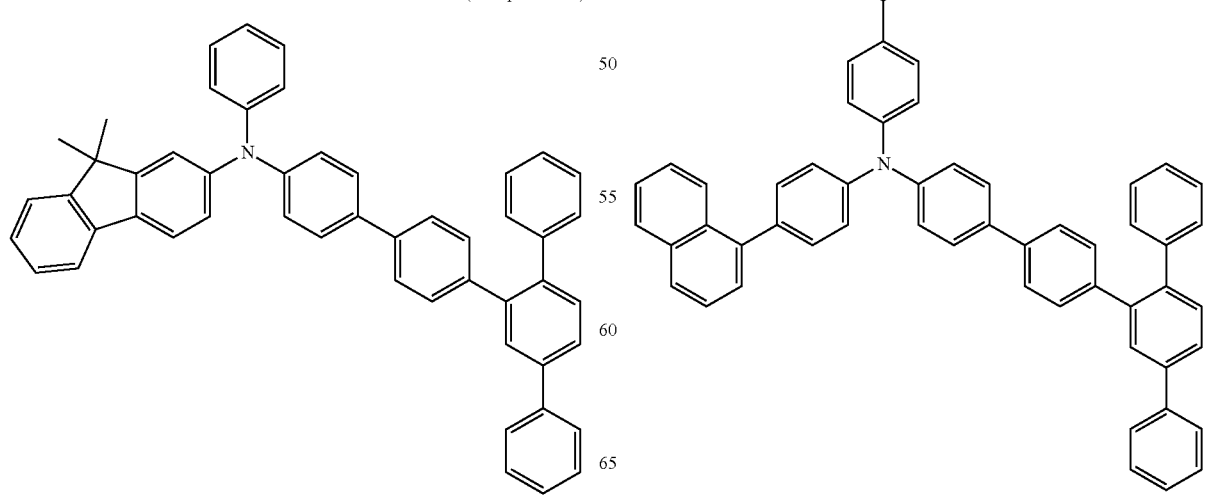

(Compound-74)
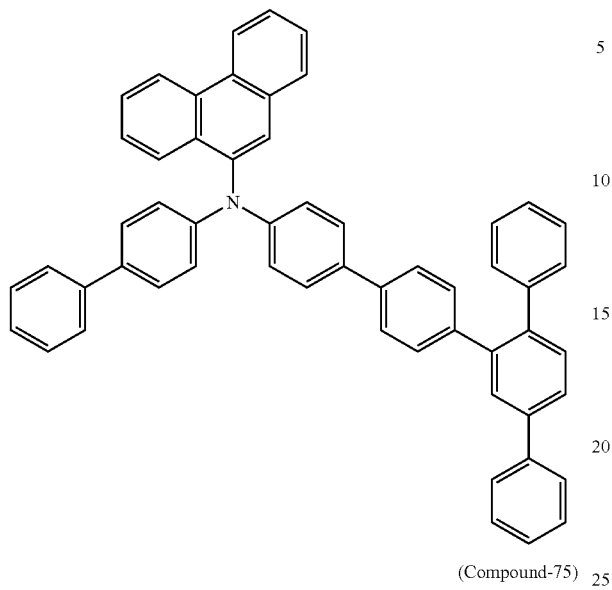
(Compound-75)
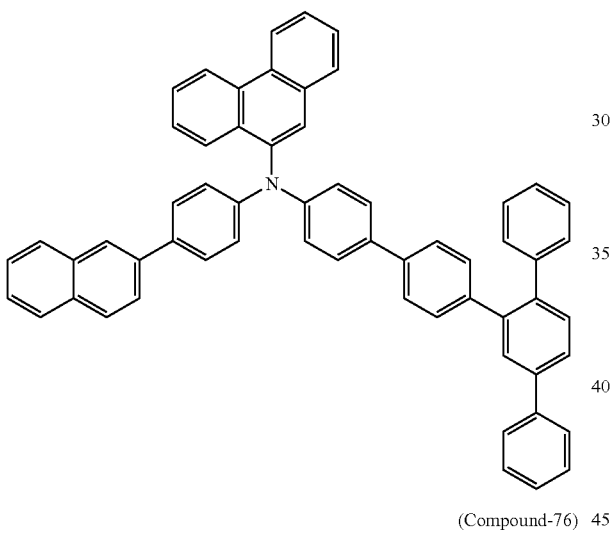
(Compound-76)
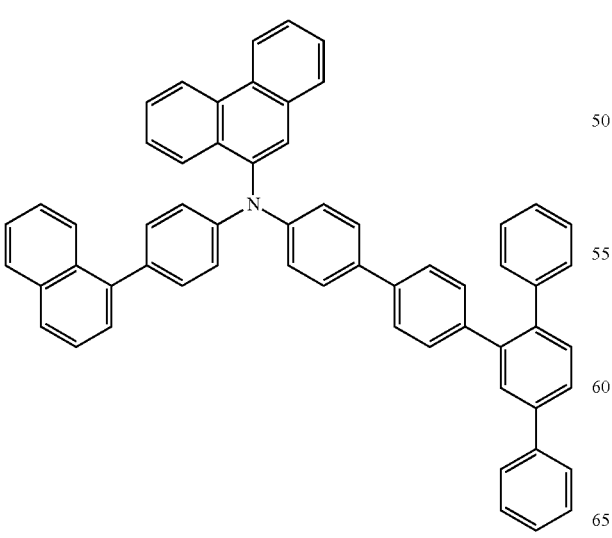
(Compound-77)
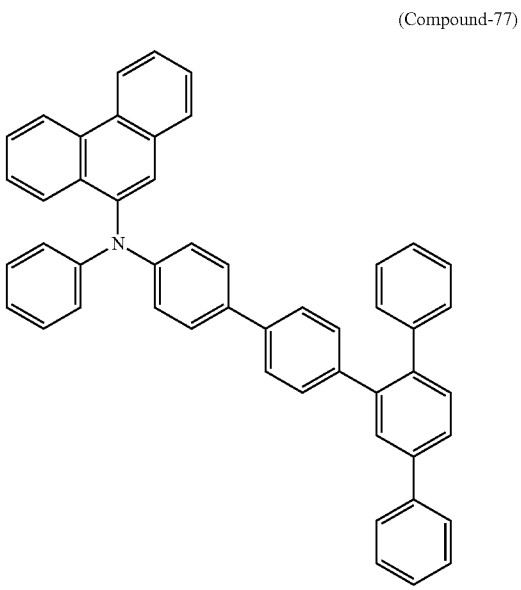
(Compound-78)
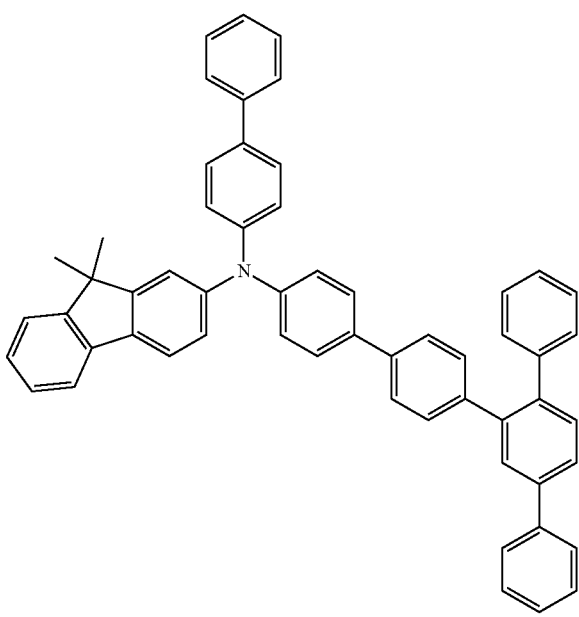

(Compound-79)
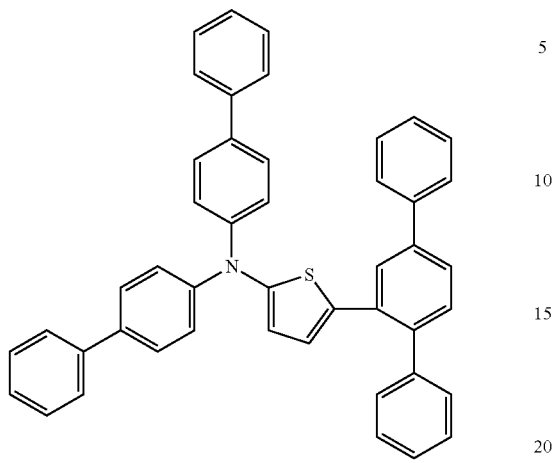
(Compound-80)
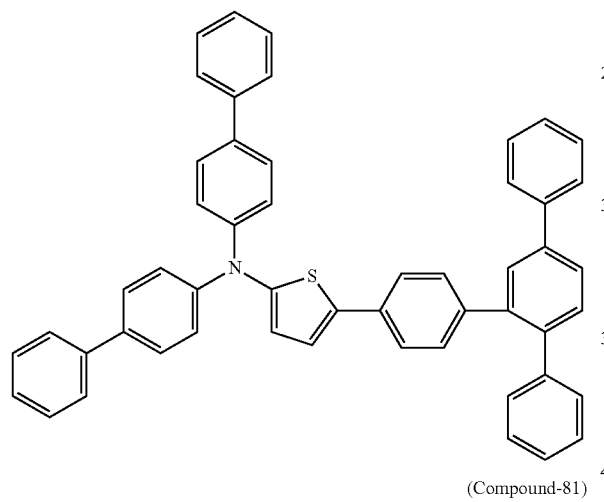
(Compound-81)
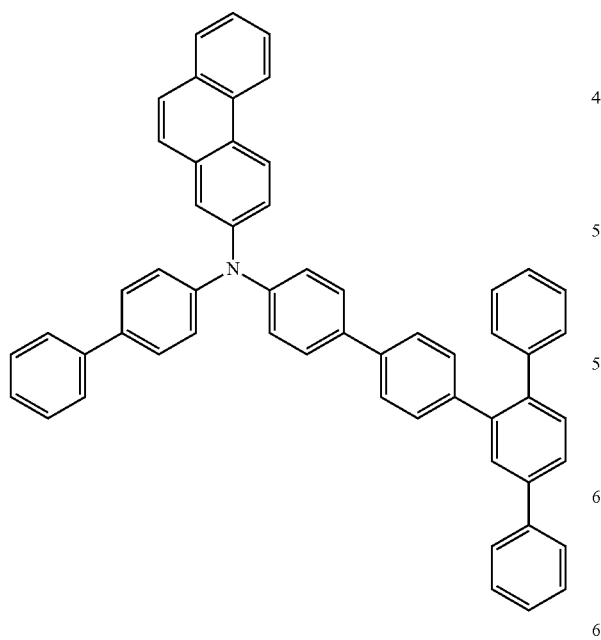
(Compound-82)
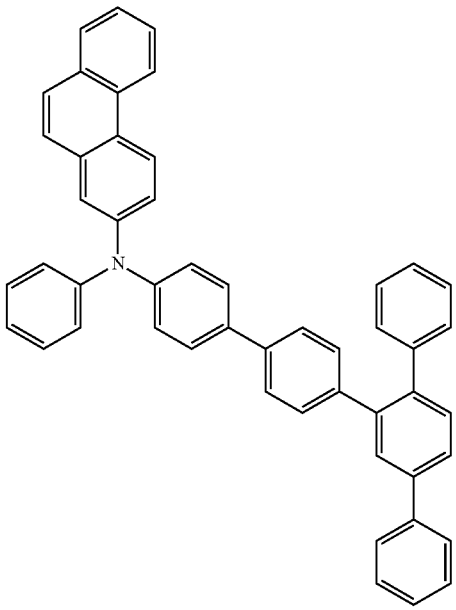
(Compound-83)
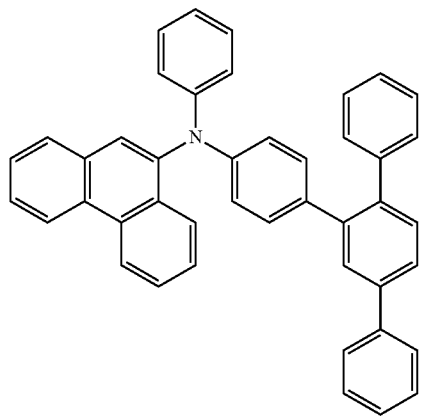
(Compound-84)
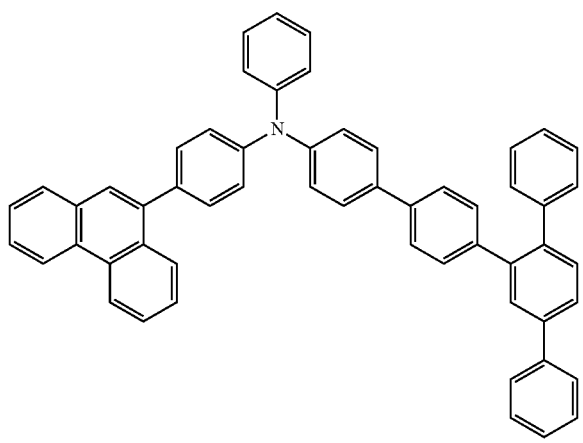

[Chem. 17]
(Compound-85)
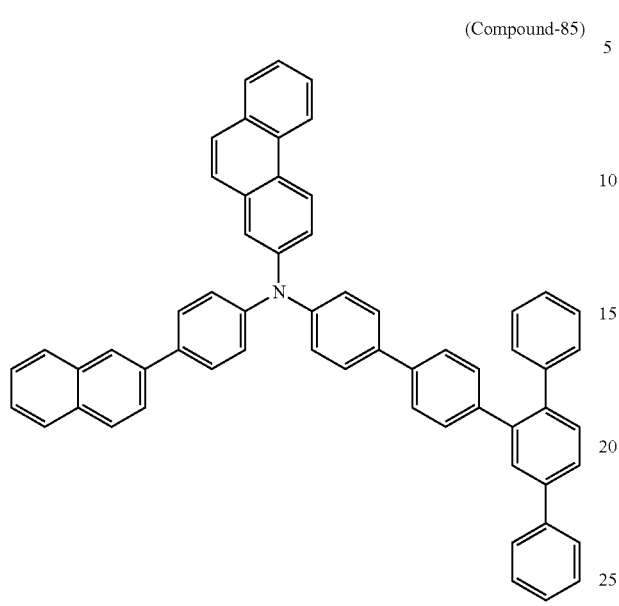
(Compound-86)
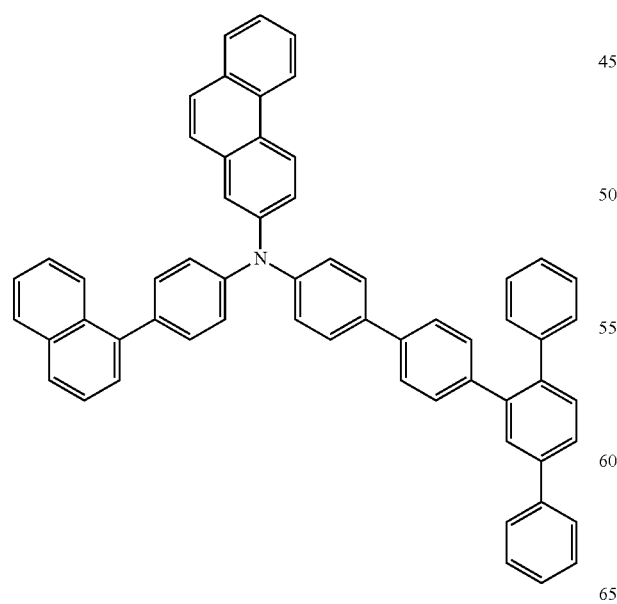
(Compound-87)
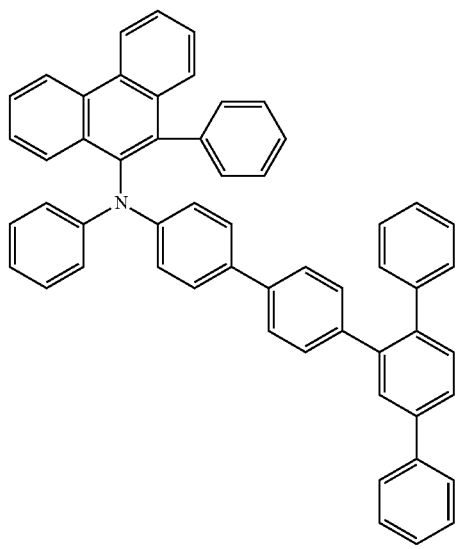
(Compound-88)
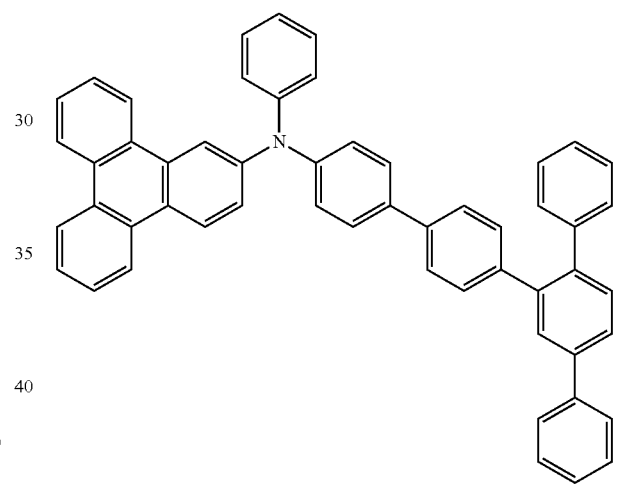
(Compound-89)
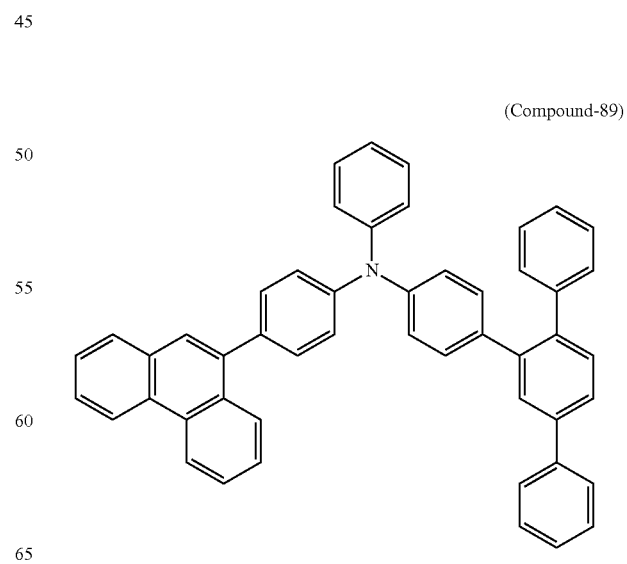

(Compound-90)

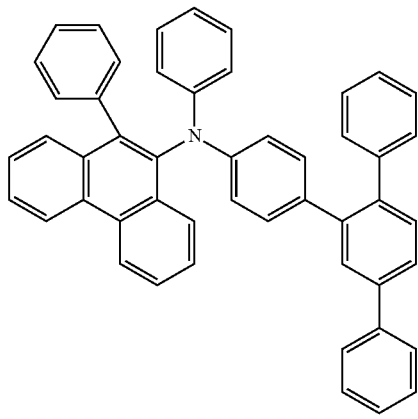

(Compound-91)

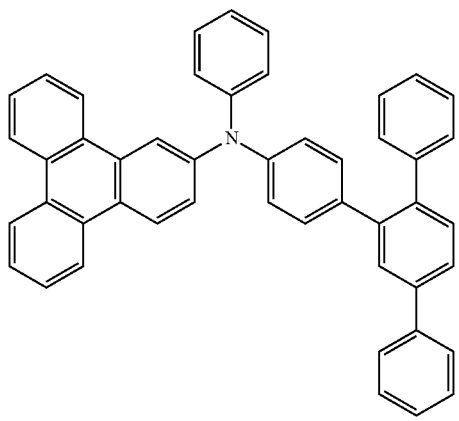

The compound having a triarylamine structure and being represented by the general formula (A-1) can be purified using a known method that is used to purify an organic compound, such as purification through column chromatography, purification through adsorption using silica gel, activated carbon, activated clay, or the like, recrystallization or crystallization using a solvent, or purification through sublimation. Identification of the compound can be performed using NMR analysis or the like. It is preferable to measure the melting point, the glass transition point (Tg), and the work function as physical properties. The melting point is an indicator of the vapor deposition properties. The glass transition point (Tg) is an indicator of the stability in a thin film state. The work function is an indicator of the hole transportability and the electron blockability.

The melting point and the glass transition point (Tg) can be measured using, for example, a powder and a high-sensitivity differential scanning calorimeter (DSC3100SA manufactured by Bruker AXS K.K.).

The work function can be obtained by, for example, forming a 100-nm thin film on an ITO substrate and performing the measurement using an ionization potential measuring device (PYS-202 manufactured by Sumitomo Heavy Industries, Ltd.).

The organic EL device of the present invention may have a structure in which an anode, a hole injection layer, a hole transport layer, a light emitting layer, an electron transport layer, an electron injection layer, and a cathode are sequentially formed on a substrate; a structure in which an electron blocking layer is further provided between the hole transport layer and the light emitting layer; or a structure in which a hole blocking layer is further provided between the light emitting layer and the electron transport layer. In these multilayer structures, a single organic layer can perform the functions of several layers. For example, a configuration in which a single organic layer serves as both the hole injection layer and the hole transport layer, a configuration in which a single organic layer serves as both the electron injection layer and the electron transport layer, and the like may also be adopted. Moreover, it is possible to stack two or more organic layers having the same function, and a configuration in which two hole transport layers are stacked, a configuration in which two light emitting layers are stacked, a configuration in which two electron transport layers are stacked, and the like may also be adopted.

For example, FIG. 1 shows a layer configuration of an organic EL device in which an anode 2, a hole injection layer 3, a hole transport layer 4, an electron blocking layer 5, a light emitting layer 6, an electron transport layer 7, an electron injection layer 8, and a cathode 9 are formed in this order on a glass substrate 1. Hereinafter, the various layers constituting the organic EL device of the present invention will be described.

(Anode 2)

An electrode material having a high work function, such as ITO or gold, is used for the anode 2.

(Hole Injection Layer 3)

In addition to the compound having a triarylamine structure of the present invention, known compounds can be used for the hole injection layer 3, and examples thereof include: porphyrin compounds typified by copper phthalocyanine; starburst triphenylamine derivatives; arylamine compounds having a structure containing two or more triphenylamine structures or carbazolyl structures in the molecule, the triphenylamine or the carbazolyl structures being linked via a single bond or a divalent group having no heteroatom; and the like. It is also possible to use acceptor type heterocyclic compounds such as hexacyanoazatriphenylene, and coating type polymer materials such as poly(3,4-ethylenedioxythiophene) (hereinafter abbreviated as PEDOT)/poly(styrenesulfonate) (hereinafter abbreviated as PSS).

These compounds and materials may be used alone, or as a mixture of two or more, to form a hole injection layer. In the case where a mixture of two or more of these compounds and materials is used to form a hole injection layer, a compound or material that is p-doped with trisbromophenylamine hexachloroantimony, a radialene derivative (see Patent Literature 5, for example), or the like; a polymer compound having the structure of a benzidine derivative, such as N,N'-diphenyl-N,N'-di(m-tolyl)-benzidine (hereinafter abbreviated as TPD), in a partial structure thereof; or the like may be used as one component of the mixture.

With these compounds and materials, a thin film can be formed using vapor deposition, or another known method such as spin coating or inkjet printing.

(Hole Transport Layer 4)

In addition to the compound having a triarylamine structure of the present invention, known compounds having hole transportability can also be used for the hole transport layer 4. Examples of the known compounds having hole transportability include benzidine derivatives such as TPD, NPD, and N,N,N',N'-tetrabiphenylyl benzidine; 1,1-bis[(di-4-tolylamino)phenyl]cyclohexane (hereinafter abbreviated as TAPC); and arylamine compounds having a structure containing two or more triphenylamine structures or carbazolyl structures in the molecule, the triphenylamine or the carbazolyl structures being linked via a single bond or a divalent group having no heteroatom. Moreover, coating type polymer materials such as PEDOT and PSS described above can also be used. These compounds and materials may be used alone, or as a mixture of two or more, to form a hole transport layer, and the formed layers can each be used as a single layer. The hole transport layer 4 may have a structure in which layers that are each formed using one of the above-listed compounds and materials alone are stacked, a structure in which layers that are each formed using a mixture of two or more of the above-listed compounds and materials are stacked, or a structure in which a layer that is formed using one of the above-listed compounds and materials alone and a layer that is formed using a mixture of two or more of the above-listed compounds and materials are stacked. With these compounds and materials, a thin film can be formed using vapor deposition, or another known method such as spin coating or inkjet printing.

Moreover, in addition to normally used compounds and materials, a compound or material that is p-doped with trisbromophenylamine hexachloroantimony, a radialene derivative (see Patent Literature 5, for example), or the like; a polymer compound having the structure of a benzidine derivative, such as TPD, in a partial structure thereof; and the like may further be used for the hole transport layer 4.

(Electron Blocking Layer 5)

In addition to the compound having a triarylamine structure of the present invention, known compounds having an electron blocking effect can also be used for the electron blocking layer 5. Examples of the known compounds having an electron blocking effect include compounds having an electron blocking effect, such as carbazole derivatives such as 4,4',4''-tri(N-carbazolyl)triphenylamine (hereinafter abbreviated as TCTA), 9,9-bis[4-(carbazole-9-yl)phenyl] fluorene, 1,3-bis(carbazole-9-yl)benzene (hereinafter abbreviated as mCP), and 2,2-bis(4-carbazole-9-ylphenyl)adamantane (hereinafter abbreviated as Ad-Cz); and compounds that have a triphenylsilyl group and a triarylamine structure and are typified by 9-[4-(carbazole-9-yl)phenyl]-9-[4-(triphenyl silyl)phenyl]-9H-fluorene. These compounds and materials may be used alone, or as a mixture of two or more, to form an electron blocking layer, and the formed layers can each be used as a single layer. The electron blocking layer 5 may have a structure in which layers that are each formed using one of the above-listed materials alone are stacked, a structure in which layers that are each formed using a mixture of two or more of the above-listed materials are stacked, or a structure in which a layer that is formed using one of the above-listed materials alone and a layer that is formed using a mixture of two or more of the above-listed materials are stacked. With these compounds, a thin film can be formed using vapor deposition, or another known method such as spin coating or inkjet printing.

(Light Emitting Layer 6)

In addition to the compound having a triarylamine structure of the present invention, known light emitting materials can also be used for the light emitting layer 6. Examples of the known light emitting materials include metal complexes of quinolinol derivatives such as $Alq_3$, various types of metal complexes, an anthracene derivative, a bisstyrylbenzene derivative, a pyrene derivative, an oxazole derivative, and a poly(p-phenylene vinylene derivative). Moreover, the light emitting layer 6 may also be formed using a host material and a dopant material. As the host material, an anthracene derivative is preferably used. In addition, the above-listed light emitting materials including the compound having a triarylamine structure of the present invention, as well as a heterocyclic compound having an indole ring as a partial structure of a fused ring, a heterocyclic compound having a carbazole ring as a partial structure of a fused ring, a carbazole derivative, a thiazole derivative, a benzimidazole derivative, a polydialkylfluorene derivative, and the like can be used as the host material. As the dopant material, quinacridone, coumalin, rubrene, perylene, and derivatives thereof; a benzopyran derivative; a rhodamine derivative; an aminostyryl derivative; and the like may be used. These compounds and materials may be used alone, or as a mixture of two or more, to form a light emitting layer, and the formed layers can each be used as a single layer. The light emitting layer 6 may have a structure in which layers that are each formed using one of the above-listed compounds and materials alone are stacked, a structure in which layers that are each formed using a mixture of two or more of the above-listed compounds and materials are stacked, or a structure in which a layer that is formed using one of the above-listed compounds and materials alone and a layer that is formed using a mixture of two or more of the above-listed compounds and materials are stacked.

Moreover, a phosphorescent emitter can also be used as a light emitting material. As the phosphorescent emitter, a phosphorescent emitter of a metal complex of iridium, platinum, or the like can be used. Examples include a green phosphorescent emitter such as $Ir(ppy)_3$, a blue phosphorescent emitter such as Flrpic or Flr6, and a red phosphorescent emitter such as $Btp_2Ir$ (acac). In this case, host materials having hole injectability and transportability, such as carbazole derivatives such as 4,4'-di(N-carbazolyl)biphenyl (hereinafter abbreviated as CBP), TCTA, and mCP, as well as compounds having a benzazole ring structure and a pyridoindole ring structure, may be used as the host material. Also, host materials having electron transportability, such as p-bis(triphenylsilyl)benzene (hereinafter abbreviated as UGH2) and 2,2',2''-(1,3,5-phenylene)-tris(1-phenyl-1H-benzimidazole) (hereinafter abbreviated as TPBI), may be used as the host material. When a phosphorescent emitter such as those listed above is used as the light emitting material, a high-performance organic EL device can be produced.

In order to avoid concentration quenching, it is preferable that doping of the host material with a phosphorescent light emitting material is performed within a range of 1 to 30 wt % with respect to the entire light emitting layer, and it is preferable to perform the doping through co-deposition.

As the light emitting material, a material that emits delayed fluorescence such as a CDCB derivative, specifically, PIC-TRZ, CC2TA, PXZ-TRZ, 4CzIPN, or the like can also be used (see Non-Patent Literature 3, for example). With these materials, a thin film can be formed using vapor deposition, or another known method such as spin coating or inkjet printing.

(Hole Blocking Layer)

A hole blocking layer (not shown in FIG. 1) may be provided between the light emitting layer 6 and the electron transport layer 7. A known compound having a hole blocking effect can be used for the hole blocking layer. Examples of the known compound having a hole blocking effect include a phenanthroline derivative, such as bathocuproine (hereinafter abbreviated as BCP); a metal complex of a quinolinol derivative, such as aluminum (III) bis(2-methyl-8-quinolinate)-4-phenylphenolate (hereinafter abbreviated as BAlq); various types of rare-earth complexes; an oxazole derivative; a triazole derivative; a triazine derivative; a pyrimidine derivative; an oxadiazole derivative; a benzazole derivative; and the like. These compounds may also serve as the material of the electron transport layer. These compounds may be used alone, or as a mixture of two or more, to form a hole blocking layer, and the formed layers can each be used as a single layer. The hole blocking layer may have a structure in which layers that are each formed using one of the above-listed compounds alone are stacked, a structure in which layers that are each formed using a mixture of two or more of the above-listed compounds are stacked, or a structure in which a layer that is formed using one of the above-listed compounds alone and a layer that is formed using a mixture of two or more of the above-listed compounds are stacked. With these materials, a thin film can be formed using vapor deposition, or another known method such as spin coating or inkjet printing.

(Electron Transport Layer 7)

A known compound having electron transportability can be used for the electron transport layer 7. Examples of the known compound having electron transportability include metal complexes of quinolinol derivatives, such as $Alq_3$ and BAlq; various types of metal complexes; a triazole derivative; a triazine derivative; a pyrimidine derivative; an oxadiazole derivative; a pyridine derivative; a benzimidazole derivative; a benzazole derivative; a thiadiazole derivative; an anthracene derivative; a carbodiimide derivative; a quinoxaline derivative; a pyridoindole derivative; a phenanthroline derivative; a silole derivative; and the like. These compounds may be used alone, or as a mixture of two or more, to form an electron transport layer, and the formed layers can each be used as a single layer. The electron transport layer may have a structure in which layers that are each formed using one of the above-listed compounds alone are stacked, a structure in which layers that are each formed using a mixture of two or more of the above-listed compounds are stacked, or a structure in which a layer that is formed using one of the above-listed compounds alone and a layer that is formed using a mixture of two or more of the above-listed compounds are stacked. With these materials, a thin film can be formed using vapor deposition, or another known method such as spin coating or inkjet printing.

(Electron Injection Layer 8)

An alkali metal salt such as lithium fluoride or cesium fluoride; an alkaline earth metal salt such as magnesium fluoride; a metal complex of a quinolinol derivative such as lithium quinolinol; a metal oxide such as aluminum oxide; or a metal such as ytterbium (Yb), samarium (Sm), calcium (Ca), strontium (Sr), or cesium (Cs) can be used for the electron injection layer 8. The electron injection layer 8 can be omitted by selecting a suitable combination of the electron transport layer and the cathode.

Furthermore, for the electron injection layer 8 and the electron transport layer 7, a material obtained by n-doping a material normally used for those layers with a metal such as cesium can be used.

(Cathode 9)

An electrode material having a low work function, such as aluminum; an alloy having an even lower work function, such as a magnesium-silver alloy, a magnesium-calcium alloy, a magnesium-indium alloy, or an aluminum-magnesium alloy; or an electrode material, such as ITO or IZO, is used for the cathode 9.

EXAMPLES

Hereinafter, embodiments of the present invention will be described in greater detail using examples. However, the present invention is not limited to the examples below without departing from the gist thereof.

Example 1

Synthesis of N,N-bis([1,1'-biphenyl]-4-yl)-5'-phenyl-(1,1':2',1''-triphenyl)-4-amine (Compound-1)

First, 5.00 g of bis(4-biphenylyl)amine, 6.59 g of 4-bromo-5'-phenyl-1,1':2',1''-terphenyl, 50 ml of toluene, 1.79 g of sodium t-butoxide, 0.13 g of t-butylphosphine (50 wt % toluene solution), and 0.07 g of palladium (II) acetate were added to a nitrogen-purged reaction vessel and stirred for 3 hours under heat reflux. Next, 10 g each of silica gel and activated clay were added to the reaction liquid, which was then stirred for 10 minutes and subsequently subjected to Celite filtration at 80° C. Then, crystallization was performed by adding 180 ml of acetone to the concentrated filtrate, and a solid was thus obtained. The obtained solid was purified by column chromatography using an n-heptane/dichloromethane mixed solvent. The concentrated solid was dissolved in 20 ml of dichloromethane, and a crystallization operation was then performed by adding 200 ml of n-heptane. Thus, 5.4 g (with a yield of 56%) of a white solid of N,N-bis([1,1'-biphenyl]-4-yl)-5'-phenyl-(1,1':2',1''-triphenyl)-4-amine (Compound-1) was obtained.

[Chem. 18]

(Compound-1)

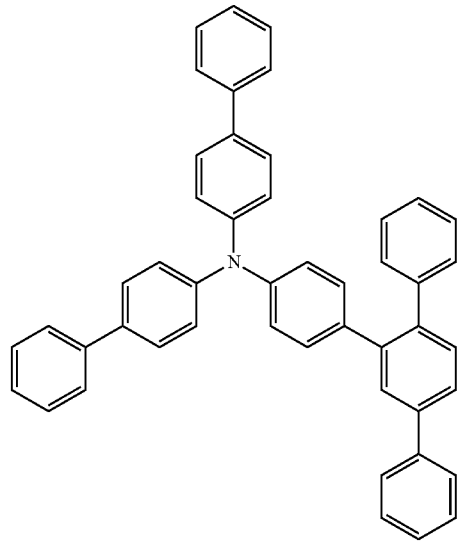

The structure of the obtained white solid was identified using NMR.

In $^1$H-NMR (DMSO-$d_6$), the following signals of 35 hydrogens were detected.

δ (ppm)=7.80-7.72 (4H), 7.67-7.62 (8H), 7.53-7.40 (8H), 7.36-7.28 (5H), 7.21-7.09 (8H), 6.98 (2H)

Example 2

Synthesis of N-([1,1'-biphenyl]-4-yl)-9,9-dimethyl-N-(5'-phenyl-[1,1':2',1''-triphenyl]-4-yl)-9H-fluorene-2-amine (Compound-2)

First, 6.10 g of 2-(4-biphenylyl)amino-9,9-dimethylfluorene, 7.15 g of 4-bromo-5'-phenyl-1,1':2',1''-terphenyl, 61 ml of toluene, 1.95 g of sodium t-butoxide, 0.14 g of t-butylphosphine (50 wt % toluene solution), and 0.08 g of palladium (II) acetate were added to a nitrogen-purged reaction vessel and stirred for 3 hours under heat reflux. Next, 10 g each of silica gel and activated clay were added to the reaction liquid, which was then stirred for 10 minutes and subsequently subjected to Celite filtration at 80° C. Then, a crystallization operation was performed by adding 220 ml of acetone to the concentrated filtrate, and a solid was thus obtained. The obtained solid was purified by column chromatography using an n-heptane/dichloromethane mixed solvent. The concentrated solid was dissolved in 22 ml of dichloromethane, and a crystallization operation was then performed by adding 220 ml of n-heptane. A similar crystallization operation was performed again. Thus, 2.2 g (with a yield of 19%) of a white solid of N-([1,1'-biphenyl]-4-yl)-9,9-dimethyl-N-(5'-phenyl-[1,1':2',1''-triphenyl]-4-yl)-9H-fluor ene-2-amine (Compound-2) was obtained.

[Chem. 19]

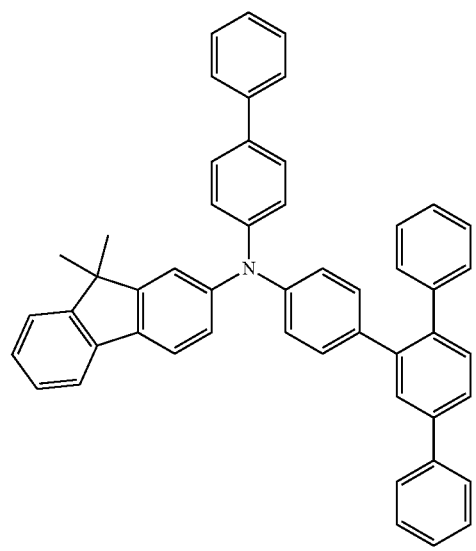

(Compound-2)

The structure of the obtained white solid was identified using NMR.

In $^1$H-NMR (DMSO-$d_6$), the following signals of 39 hydrogens were detected.

δ (ppm)=7.73-7.56 (10H), 7.49-7.42 (10H), 7.35-7.22 (6H), 7.11-7.07 (4H), 6.98-6.96 (3H)

Example 3

Synthesis of N,N-bis(4-[naphthalene-1-yl]phenyl)-5'-phenyl-(1,1':2',1''-triphenyl)-4-amine (Compound-3)

First, 9.00 g of N,N-bis[4-(naphthalene-1-yl)phenyl] amine, 9.87 g of 4-bromo-5'-phenyl-1,1':2',1''-terphenyl, 90 ml of toluene, 2.46 g of sodium t-butoxide, 0.17 g of t-butylphosphine (50 wt % toluene solution), and 0.10 g of palladium (II) acetate were added to a nitrogen-purged reaction vessel and stirred for 3 hours under heat reflux. Next, 15 g each of silica gel and activated clay were added to the reaction liquid, which was then stirred for 10 minutes and subsequently subjected to Celite filtration at 80° C. The filtrate was concentrated, and then purified by column chromatography using an n-heptane/dichloromethane mixed solvent. The concentrated solid was dissolved in 30 ml of dichloromethane, which was then added dropwise to 300 ml of methanol, and a solid was thus obtained. The obtained solid was purified in a similar manner. Thus, 13.0 g (with a yield of 83.9%) of a white solid of N,N-bis(4-[naphthalene-1-yl]phenyl)-5'-phenyl-(1,1':2',1''-triphenyl)-4-amine (Compound-3) was obtained.

[Chem. 20]

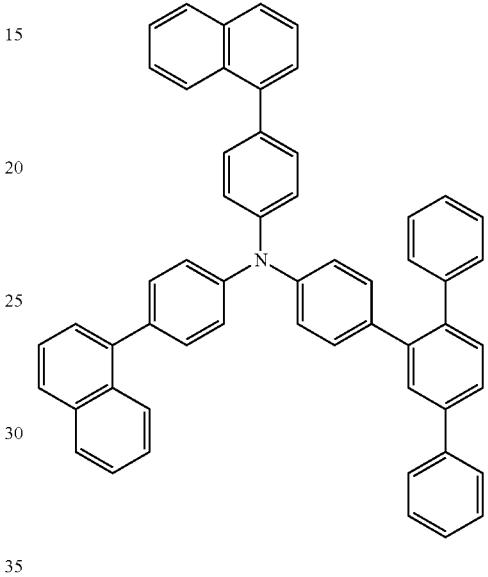

(Compound-3)

The structure of the obtained white solid was identified using NMR.

In $^1$H-NMR (DMSO-$d_6$), the following signals of 39 hydrogens were detected.

δ (ppm)=8.02-7.94 (6H), 7.82-7.75 (4H), 7.64-7.47 (15H), 7.43-7.21 (12H), 7.16-7.10 (2H)

Example 4

Synthesis of N,N-bis(4-[naphthalene-2-yl]phenyl)-5'-phenyl-(1,1':2',1''-triphenyl)-4-amine (Compound-4)

First, 10.00 g of N,N-bis[4-(naphthalene-2-yl)phenyl] amine, 10.97 g of 4-bromo-5'-phenyl-1,1':2',1''-terphenyl, 100 ml of toluene, 2.74 g of sodium t-butoxide, 0.19 g of t-butylphosphine (50 wt % toluene solution), and 0.11 g of palladium (II) acetate were added to a nitrogen-purged reaction vessel and stirred for 3 hours under heat reflux. Next, 17 g each of silica gel and activated clay were added to the reaction liquid, which was then stirred for 10 minutes and subsequently subjected to Celite filtration at 80° C. Then, a crystallization operation was performed by adding 340 ml of acetone to the concentrated filtrate, and a solid was thus obtained. The obtained solid was dissolved in 34 ml of toluene, and a crystallization operation was then performed by adding 340 ml of acetone. Thus, 8.3 g (with a yield of 48%) of a white solid of N,N-bis(4-[naphthalene-2-yl]phenyl)-5'-phenyl-(1,1':2',1''-triphenyl)-4-amine (Compound-4) was obtained.

[Chem. 21]

(Compound-4)

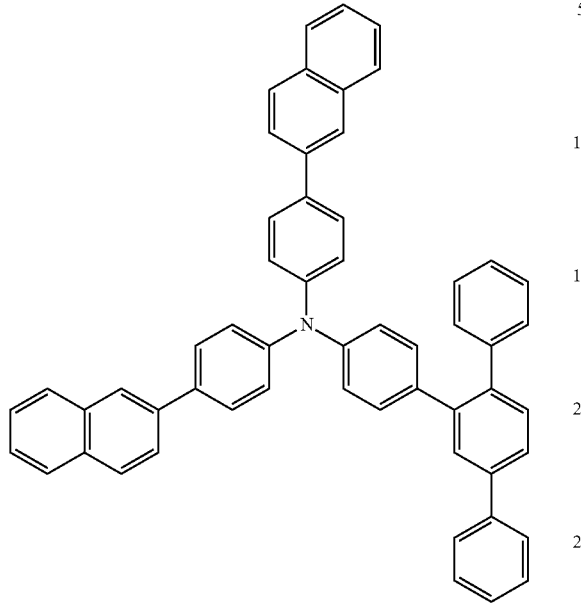

[Chem. 22]

(Compound-58)

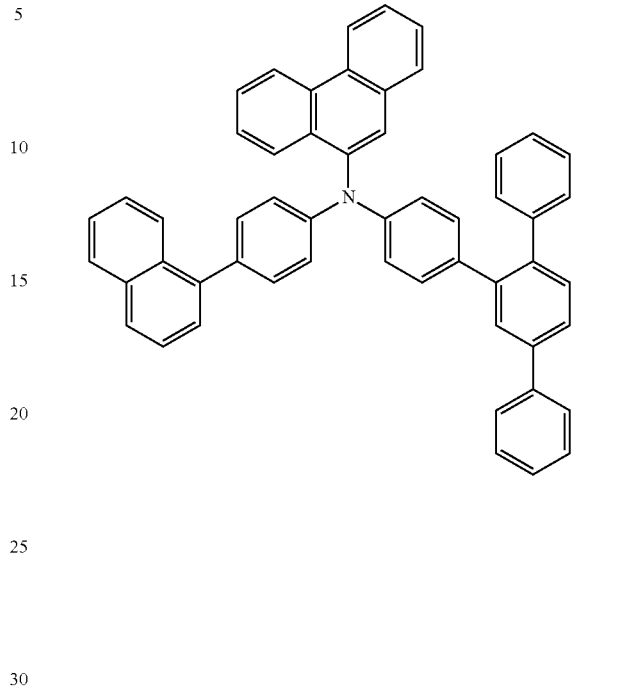

The structure of the obtained white solid was identified using NMR.

In $^1$H-NMR (DMSO-d$_6$), the following signals of 39 hydrogens were detected.

δ (ppm)=8.21 (2H), 8.01-7.92 (6H), 7.88-7.74 (10H), 7.57-7.48 (7H), 7.43-7.30 (4H), 7.28-7.17 (8H), 7.03 (2H)

Example 5

Synthesis of N-(4-(naphthalene-1-yl)phenyl)-N-(5'-phenyl[1,1':2',1''-terphenyl]-4-yl)phenanthrene-9-amine (Compound-58)

First, 8.5 g of N-(4-(naphthalene-1-yl)phenyl)-N-(5'-phenyl[1,1':2',1''-terphenyl]-4-amine, 4.8 g of 9-bromophenanthrene, 85 ml of toluene, 2.3 g of sodium t-butoxide, 0.3 g of t-butylphosphine (50 wt % toluene solution), and 0.1 g of palladium (II) acetate were added to a nitrogen-purged reaction vessel and stirred for 3 hours under heat reflux. Celite filtration was performed at 80° C. Activated clay and silica gel were added to the filtrate, and purification through adsorption was then performed. The filtrate was concentrated, and the residue was crystalized using acetone. Thus, 8.3 g (with a yield of 73%) of a white solid of N-(4-(naphthalene-1-yl)phenyl)-N-(5'-phenyl[1,1':2',1''-terphenyl]-4-yl)phenanthrene-9-amine (Compound-58) was obtained.

The structure of the obtained white solid was identified using NMR.

In $^1$H-NMR (CDCl$_3$), the following signals of 37 hydrogens were detected.

δ (ppm)=8.75-8.84 (2H), 8.16-8.20 (1H), 8.05-8.09 (1H), 7.91-7.95 (3H), 7.12-7.78 (3 OH)

Example 6

Synthesis of N-(4-(naphthalene-2-yl)phenyl)-N-(5'-phenyl[1,1':2',1''-terphenyl]-4-yl)phenanthrene-9-amine (Compound-59)

First, 8.0 g of N-(4-(naphthalene-2-yl)phenyl)-N-(5'-phenyl[1,1':2',1''-terphenyl]-4-amine, 4.5 g of 9-bromophenanthrene, 80 ml of toluene, 2.2 g of sodium t-butoxide, 0.2 g of t-butylphosphine (50 wt % toluene solution), and 0.1 g of palladium (II) acetate were added to a nitrogen-purged reaction vessel and stirred for 3 hours under heat reflux. Celite filtration was performed at 80° C. Activated clay and silica gel were added to the filtrate, and purification through adsorption was then performed. The filtrate was concentrated, and the residue was crystalized using toluene-acetone. Thus, 6.6 g (with a yield of 62%) of a white solid of N-((4-naphthalene-2-yl)phenyl)-N-(5'-phenyl[1,1':2',1''-terphenyl]-4-yl)phenanthrene-9-amine (Compound-59) was obtained.

[Chem. 23]

(Compound-59)

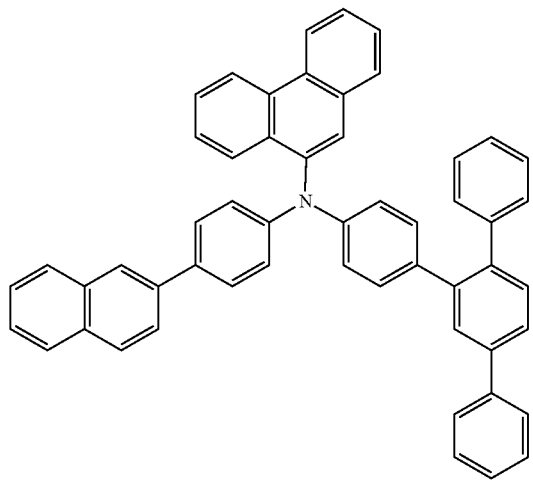

[Chem. 24]

(Compound-71)

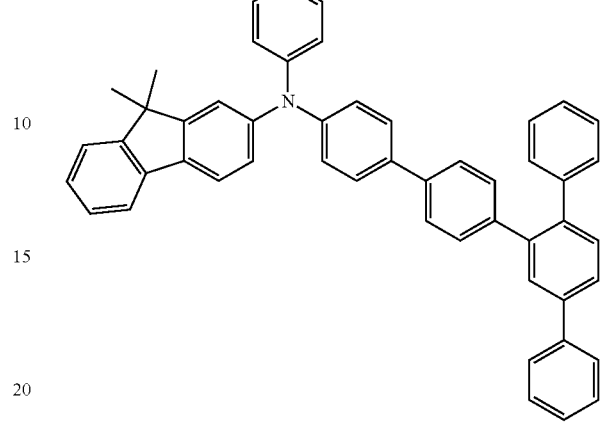

The structure of the obtained white solid was identified using NMR.

In $^1$H-NMR (CDCl$_3$), the following signals of 37 hydrogens were detected.

δ (ppm)=8.74-8.83 (2H), 8.12-8.17 (1H), 8.30 (1H), 7.21-7.94 (29H), 7.08-7.14 (4H)

Example 7

Synthesis of 9,9-dimethyl-N-phenyl-N-(4'-phenyl[1,1':2',1":4",1'''-quaterphenyl]-4"-yl)-9H-fluorene-2-amine (Compound-71)

First, 4.5 g of 9,9-dimethyl-N-phenyl-9H-fluorene-2-amine, 7.6 g of 4"-bromo4'-phenyl-[1,1':2',1":4",1'''-quaterphenyl], 45 ml of toluene, 1.8 g of sodium t-butoxide, 0.13 g of t-butylphosphine (50 wt % toluene solution), and 0.07 g of palladium (II) acetate were added to a nitrogen-purged reaction vessel and stirred overnight under heat reflux. The reaction liquid was cooled to room temperature, washed with water, and dried over anhydrous magnesium sulfate. The desiccant was removed by filtration, and the filtrate was concentrated. The residue was purified by column chromatography.

Thus, 6.5 g (with a yield of 62%) of a white solid of 9,9-dimethyl-N-phenyl-N-(4'-phenyl[1,1':2',1":4",1'''-quaterphenyl]-4"-yl)-9H-fluorene-2-amine (Compound-71) was obtained.

The structure of the obtained white solid was identified using NMR.

In $^1$H-NMR (CDCl$_3$), the following signals of 39 hydrogens were detected.

δ (ppm)=7.51-7.80 (13H), 7.22-7.48 (18H), 7.08-7.16 (2H), 1.50 (6H)

Example 8

Synthesis of N-([1,1'-biphenyl]-4-yl)-N-(4-(naphthalene-2-yl)phenyl)-4'-phenyl-[1,1':2',1":4",1'''-quaterphenyl]-4'''-amine (Compound-72)

First, 5.1 g of N-(4-(naphthalene-2-yl)phenyl)-[1,1'-biphenyl]-4-amine, 6.7 g of 4"-bromo4'-phenyl-[1,1':2',1":4", 1'''-quaterphenyl], 51 ml of toluene, 1.6 g of sodium t-butoxide, 0.11 g of t-butylphosphine (50 wt % toluene solution), and 0.06 g of palladium (II) acetate were added to a nitrogen-purged reaction vessel and stirred overnight under heat reflux. The reaction liquid was cooled to room temperature, and insoluble matter was removed by Celite filtration. Activated carbon was added to the filtrate, and purification through adsorption was then performed. The filtrate was concentrated, and the residue was crystalized using toluene-acetone. Thus, 7.6 g (with a yield of 74%) of a white solid of N-([1,1'-biphenyl]-4-yl)-N-(4-(naphthalene-2-yl)phenyl)-4-phenyl-[1,1:2',1":4",1'''-quaterphenyl]-4'''-amine (Compound-72) was obtained.

[Chem. 25]

(Compound-72)

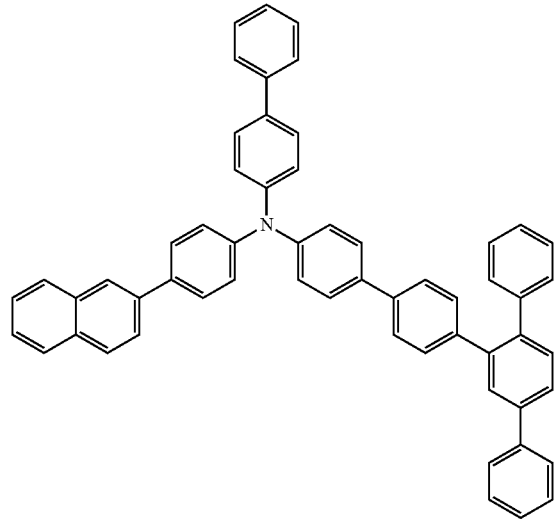

[Chem. 26]

(Compound-77)

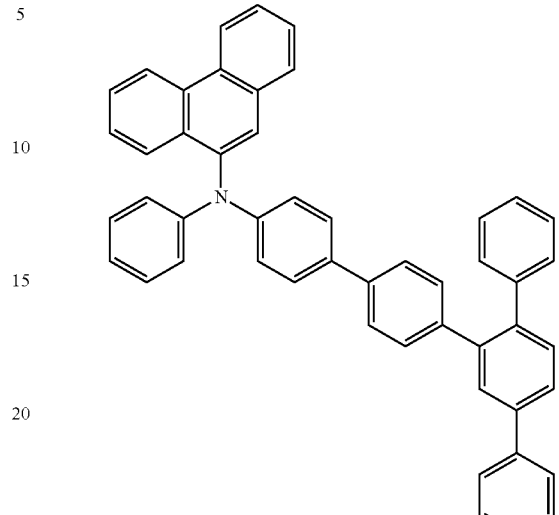

The structure of the obtained white solid was identified using NMR.

In $^1$H-NMR (CDCl$_3$), the following signals of 41 hydrogens were detected.

δ (ppm)=8.11 (1H), 7.91-7.98 (3H), 7.65-7.83 (9H), 7.28-7.62 (28H)

Example 9

Synthesis of N-phenyl-N-(4'-phenyl-[1,1':2',1":4", 1'''-quaterphenyl]-4'''-yl)phenanthrene-9-amine (Compound-77)

First, 5.0 g of N-phenyl-phenanthrene-9-amine, 9.4 g of 4"-bromo4'-phenyl-[1,1':2',1":4",1'''-quaterphenyl], 50 ml of toluene, 2.1 g of sodium t-butoxide, 0.15 g of t-butylphosphine (50 wt % toluene solution), and 0.08 g of palladium (II) acetate were added to a nitrogen-purged reaction vessel and stirred overnight under heat reflux. The reaction liquid was cooled to 80° C., and insoluble matter was removed by Celite filtration. The filtrate was concentrated, and the residue was purified by column chromatography. Thus, 3.8 g (with a yield of 32%) of a white solid of N-phenyl-N-(4'-phenyl-[1,1':2',1":4",1'''-quaterphenyl]-4'''-yl)phenanthrene-9-amine (Compound-77) was obtained.

The structure of the obtained white solid was identified using NMR.

In $^1$H-NMR (CDCl$_3$), the following signals of 35 hydrogens were detected.

δ (ppm)=8.73-8.82 (2H), 8.12-8.16 (1H), 7.40-7.83 (18H), 7.18-7.32 (13H), 7.02-7.08 (1H)

Example 10

Synthesis of N-(4-(naphthalene-1-yl)phenyl)-N-(4'-phenyl-[1,1':2',1":4", 1'''-quaterphenyl]-4'''-yl) phenanthrene-2-amine (Compound-86)

First, 6.0 g of N-(4-(naphthalene-1-yl)phenyl)-phenanthrene-2-amine, 7.3 g of 4"-bromo4'-phenyl-[1,1':2', 1":4",1'''-quaterphenyl], 60 ml of toluene, 1.7 g of sodium t-butoxide, 0.12 g of t-butylphosphine (50 wt % toluene solution), and 0.07 g of palladium (II) acetate were added to a nitrogen-purged reaction vessel and stirred overnight under heat reflux. The reaction liquid was cooled to 80° C., and insoluble matter was removed by Celite filtration. The filtrate was concentrated, and the residue was purified by column chromatography. Thus, 8.0 g (with a yield of 68%) of a yellowish white solid of N-(4-(naphthalene-1-yl)phenyl)-N-(4'-phenyl-[1,1':2',1":4",1'''-quaterphenyl]-4'''-yl) phenanthrene-2-amine (Compound-86) was obtained.

[Chem. 27]

(Compound-86)

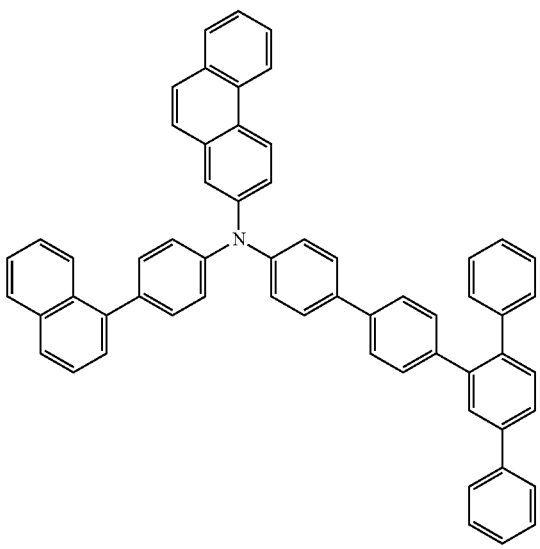

The structure of the obtained white solid was identified using NMR.

In $^1$H-NMR (CDCl$_3$), the following signals of 41 hydrogens were detected.

δ (ppm)=8.62-8.67 (2H), 8.11-8.16 (1H), 7.88-7.99 (3H), 7.27-7.79 (35H)

Example 11

The melting point and the glass transition point (Tg) of each of the compounds synthesized in the above-described examples, the compounds having a triarylamine structure and being represented by the structural formula (A-1), were measured using a high-sensitivity differential scanning calorimeter (DSC3100SA manufactured by Bruker AXS K.K.). Table 1 shows the results.

TABLE 1

| | Compound | Melting point (° C.) | Tg (° C.) |
|---|---|---|---|
| Ex. 1 | Compound-1 | — | 96.8 |
| Ex. 2 | Compound-2 | — | 102.0 |
| Ex. 3 | Compound-3 | — | 112.2 |
| Ex. 4 | Compound-4 | 220.6 | 107.1 |
| Ex. 5 | Compound-58 | — | 131.2 |
| Ex. 6 | Compound-59 | — | 129.7 |
| Ex. 7 | Compound-71 | — | 114.1 |
| Ex. 8 | Compound-72 | 228.3 | 122.0 |
| Ex. 9 | Compound-77 | — | 125.1 |
| Ex. 10 | Compound-86 | — | 139.0 |

The compounds synthesized in Examples 1 to 10, the compounds having a triarylamine structure and being represented by the structural formula (A-1), had a glass transition point of 95° C. or more, which indicated that these compounds were stable in a thin film state.

Example 12

A vapor-deposited film with a thickness of 100 nm was formed on an ITO substrate using each of the compounds synthesized in the above-described examples, the compounds having a triarylamine structure and being represented by the structural formula (A-1), and the work function was measured using an ionization potential measuring device (PYS-202 manufactured by Sumitomo Heavy Industries, Ltd.). Table 2 shows the results.

TABLE 2

| | Compound | Work function (eV) |
|---|---|---|
| Ex. 1 | Compound-1 | 5.70 |
| Ex. 2 | Compound-2 | 5.63 |
| Ex. 3 | Compound-3 | 5.73 |
| Ex. 4 | Compound-4 | 5.67 |
| Ex. 5 | Compound-58 | 5.75 |
| Ex. 6 | Compound-59 | 5.72 |
| Ex. 7 | Compound-71 | 5.65 |
| Ex. 8 | Compound-72 | 5.68 |
| Ex. 9 | Compound-77 | 5.81 |
| Ex. 10 | Compound-86 | 5.69 |

The compounds synthesized in Examples 1 to 10, the compounds having a triarylamine structure and being represented by the structural formula (A-1), each exhibited an energy level higher than 5.4 eV, which is the work function of common hole transport materials such as NPD and TPD. This means that these compounds had good hole transport capability.

The work functions of these compounds were between the work function (5.0 eV) of ITO used as the anode and the work function (6.0 eV) of the compound (EMH-1) used as the light emitting layer. This means that these compounds had good hole injection capability.

The work functions of these compounds were the values close to the work function (6.0 eV) of the compound (EMH-1) used as the light emitting layer. This means that these compounds were also favorable as the material of the light emitting layer.

Example 13

An organic EL device was prepared using the compound (Compound-1) of Example 1. The organic EL device had the configuration shown in FIG. 1, and was prepared in the following manner. An ITO electrode serving as an anode 2 was formed on a glass substrate 1 beforehand, and a hole injection layer 3, a hole transport layer 4, an electron blocking layer 5, a light emitting layer 6, an electron transport layer 7, an electron injection layer 8, and a cathode (aluminum electrode) 9 were vapor-deposited in this order on the ITO electrode.

Specifically, a glass substrate 1 on which an ITO film with a thickness of 150 nm was formed was ultrasonically cleaned in isopropyl alcohol for 20 minutes, and then dried for 10 minutes on a hot plate heated to 200° C. After that, UV/ozone treatment was performed for 15 minutes. Then, the glass substrate with ITO was attached inside a vacuum vapor deposition machine, and the pressure was reduced to 0.001 Pa or less. Subsequently, an electron acceptor (Acceptor-1) having the structural formula below and a compound (HTM-1) having the structure below were vapor-deposited so as to cover the anode 2 through binary vapor deposition at such vapor deposition rates that the ratio of the vapor deposition rate of Acceptor-1 to the vapor deposition rate of HTM-1 was 3:97, and a hole injection layer 3 with a thickness of 30 nm was thus formed. The compound (HTM-1) was formed on this hole injection layer 3 as a hole transport layer 4 with a thickness of 40 nm. The compound (Compound-1) of Example 1 was formed on this hole transport layer 4 as an electron blocking layer 5 with a thickness of 5 nm. A compound EMD-1 having the structural formula below and a compound EMH-1 having the structural formula below were vapor-deposited on this electron blocking layer 5 through binary vapor deposition at such vapor deposition rates that the ratio of the vapor deposition rate of EMD-1 to the vapor deposition rate of EMH-1 was 5:95, and a light emitting layer 6 with a thickness of 20 nm was thus formed. A compound (ETM-1) having the structural formula below and a compound (ETM-2) having the structural formula below were vapor-deposited on this light emitting layer 6 through binary vapor deposition at such vapor deposition rates that the ratio of the vapor deposition rate of ETM-1 to the vapor deposition rate of ETM-2 was 50:50, and an electron transport layer 7 with a thickness of 30 nm was thus formed. Lithium fluoride was formed on this electron transport layer 7 as an electron injection layer 8 with a thickness of 1 nm. Finally, aluminum was vapor-deposited to a thickness of 100 nm to thereby form a cathode 9. The characteristics of the prepared organic EL device were measured in the atmosphere at ordinary temperature. Table 3 collectively shows the measurement results of light emission characteristics that were obtained when a DC voltage was applied to the prepared organic EL device.

[Chem. 28]

(Acceptor-1)

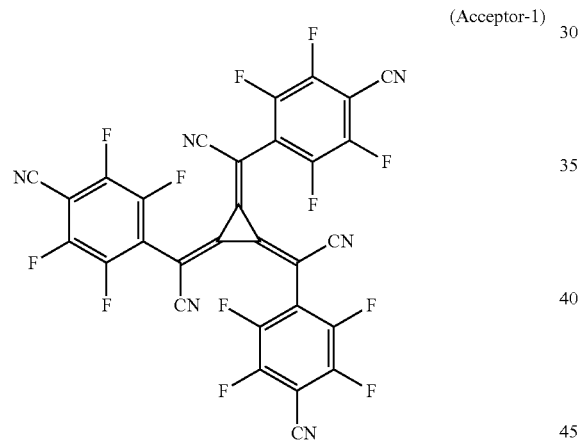

(HTM-1)

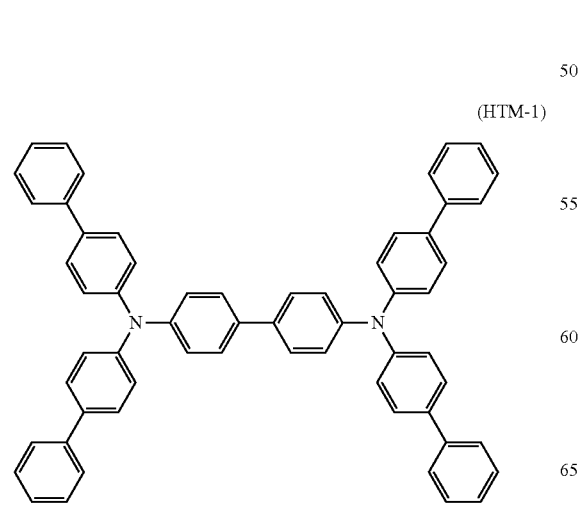

(EMD-1)

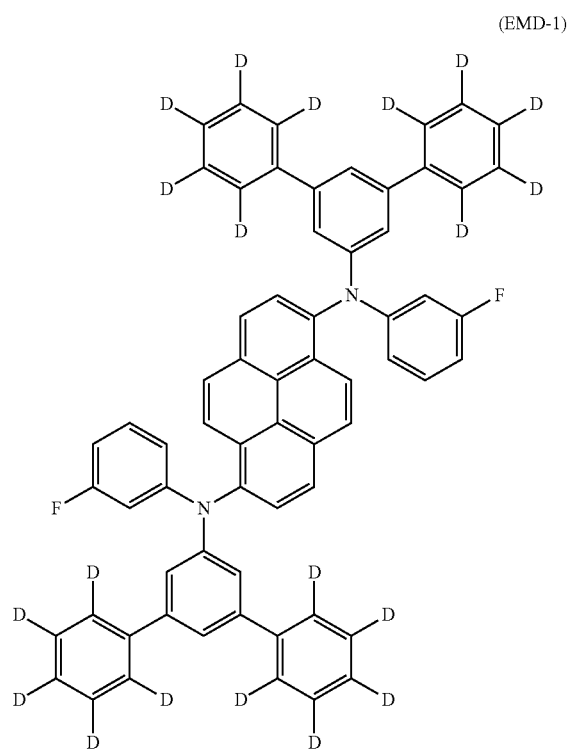

(EMH-1)

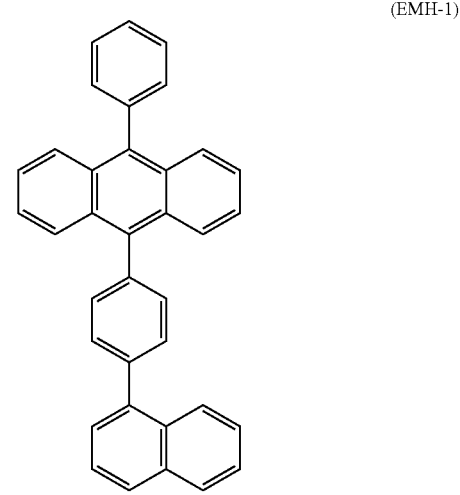

-continued

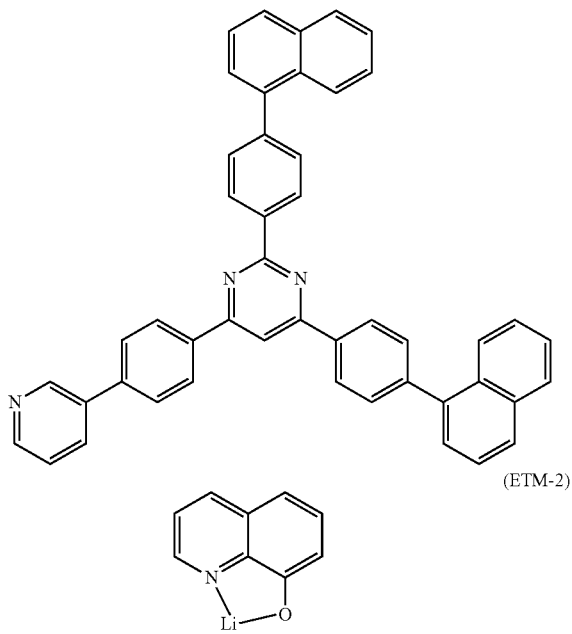

(ETM-1)

(ETM-2)

Example 14

An organic EL device was prepared under similar conditions to those of Example 13, except that the compound (Compound-1) of Example 1 serving as the material of the electron blocking layer 5 was replaced with the compound (Compound-2) of Example 2. The characteristics of the prepared organic EL device were measured in the atmosphere at ordinary temperature. Table 3 collectively shows the measurement results of light emission characteristics that were obtained when a DC voltage was applied to the prepared organic EL device.

Example 15

An organic EL device was prepared under similar conditions to those of Example 13, except that the compound (Compound-1) of Example 1 serving as the material of the electron blocking layer 5 was replaced with the compound (Compound-3) of Example 3. The characteristics of the prepared organic EL device were measured in the atmosphere at ordinary temperature. Table 3 collectively shows the measurement results of light emission characteristics that were obtained when a DC voltage was applied to the prepared organic EL device.

Example 16

An organic EL device was prepared under similar conditions to those of Example 13, except that the compound (Compound-1) of Example 1 serving as the material of the electron blocking layer 5 was replaced with the compound (Compound-4) of Example 4. The characteristics of the prepared organic EL device were measured in the atmosphere at ordinary temperature. Table 3 collectively shows the measurement results of light emission characteristics that were obtained when a DC voltage was applied to the prepared organic EL device.

Example 17

An organic EL device was prepared under similar conditions to those of Example 13, except that the compound (Compound-1) of Example 1 serving as the material of the electron blocking layer 5 was replaced with the compound (Compound-58) of Example 5. The characteristics of the prepared organic EL device were measured in the atmosphere at ordinary temperature. Table 3 collectively shows the measurement results of light emission characteristics that were obtained when a DC voltage was applied to the prepared organic EL device.

Example 18

An organic EL device was prepared under similar conditions to those of Example 13, except that the compound (Compound-1) of Example 1 serving as the material of the electron blocking layer 5 was replaced with the compound (Compound-59) of Example 6. The characteristics of the prepared organic EL device were measured in the atmosphere at ordinary temperature. Table 3 collectively shows the measurement results of light emission characteristics that were obtained when a DC voltage was applied to the prepared organic EL device.

Example 19

An organic EL device was prepared under similar conditions to those of Example 13, except that the compound (Compound-1) of Example 1 serving as the material of the electron blocking layer 5 was replaced with the compound (Compound-71) of Example 7. The characteristics of the prepared organic EL device were measured in the atmosphere at ordinary temperature. Table 3 collectively shows the measurement results of light emission characteristics that were obtained when a DC voltage was applied to the prepared organic EL device.

Example 20

An organic EL device was prepared under similar conditions to those of Example 13, except that the compound (Compound-1) of Example 1 serving as the material of the electron blocking layer 5 was replaced with the compound (Compound-72) of Example 8. The characteristics of the prepared organic EL device were measured in the atmosphere at ordinary temperature. Table 3 collectively shows the measurement results of light emission characteristics that were obtained when a DC voltage was applied to the prepared organic EL device.

Example 21

An organic EL device was prepared under similar conditions to those of Example 13, except that the compound (Compound-1) of Example 1 serving as the material of the electron blocking layer 5 was replaced with the compound (Compound-77) of Example 9. The characteristics of the prepared organic EL device were measured in the atmosphere at ordinary temperature. Table 3 collectively shows the measurement results of light emission characteristics that were obtained when a DC voltage was applied to the prepared organic EL device.

Example 22

An organic EL device was prepared under similar conditions to those of Example 13, except that the compound (Compound-1) of Example 1 serving as the material of the electron blocking layer 5 was replaced with the compound (Compound-86) of Example 10. The characteristics of the prepared organic EL device were measured in the atmosphere at ordinary temperature. Table 3 collectively shows the measurement results of light emission characteristics that were obtained when a DC voltage was applied to the prepared organic EL device.

Comparative Example 1

For comparison, an organic EL device was prepared under similar conditions to those of Example 13, except that the compound (Compound-1) of Example 1 serving as the material of the electron blocking layer 5 was replaced with HTM-1, and the electron blocking layer 5 was formed with a thickness of 5 nm. The characteristics of the prepared organic EL device were measured in the atmosphere at ordinary temperature. Table 3 collectively shows the measurement results of light emission characteristics that were obtained when a DC voltage was applied to the prepared organic EL device.

Comparative Example 2

For comparison, an organic EL device was prepared under similar conditions to those of Example 13, except that the compound (Compound-1) of Example 1 serving as the material of the electron blocking layer 5 was replaced with a compound (HTM-2) having the structural formula below. The characteristics of the prepared organic EL device were measured in the atmosphere at ordinary temperature. Table 3 collectively shows the measurement results of light emission characteristics that were obtained when a DC voltage was applied to the prepared organic EL device.

[Chem. 29]

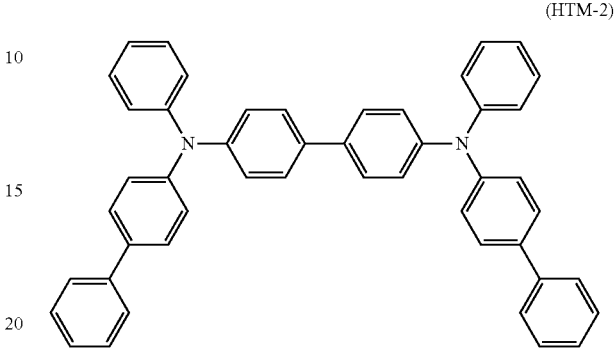

(HTM-2)

With use of the organic EL devices prepared in Examples 13 to 22 and Comparative Examples 1 and 2, the device lifespan was measured. Table 3 collectively shows the results. The device lifespan was defined as follows: when constant current driving was performed with the light emission luminance (initial luminance) when light emission started being set to 2,000 cd/m$^2$, the time taken for light emission luminance to decay to 1,900 cd/m$^2$ (corresponding to 95% of the initial luminance being set to 100%: at a decay of 95%) was measured as the device lifespan.

TABLE 3

| | Electron blocking layer | Voltage [V] (@10 mA/cm$^2$) | Luminance [cd/m$^2$] (@10 mA/cm$^2$) | Light emission efficiency [cd/A] (@10 mA/cm$^2$) | Power efficiency [lm/W] (@10 mA/cm$^2$) | Device lifespan at a decay of 95% |
|---|---|---|---|---|---|---|
| Ex. 13 | Compound-1 | 3.63 | 812 | 8.12 | 7.04 | 237 hrs. |
| Ex. 14 | Compound-2 | 3.63 | 830 | 8.30 | 7.18 | 241 hrs. |
| Ex. 15 | Compound-3 | 3.65 | 829 | 8.28 | 7.14 | 255 hrs. |
| Ex. 16 | Compound-4 | 3.63 | 832 | 8.32 | 7.21 | 247 hrs. |
| Ex. 17 | Compound-58 | 3.65 | 837 | 8.37 | 7.21 | 236 hrs. |
| Ex. 18 | Compound-59 | 3.60 | 828 | 8.28 | 7.22 | 244 hrs. |
| Ex. 19 | Compound-71 | 3.64 | 802 | 8.02 | 6.93 | 252 hrs. |
| Ex. 20 | Compound-72 | 3.62 | 800 | 8.00 | 6.93 | 257 hrs. |
| Ex. 21 | Compound-77 | 3.63 | 838 | 8.38 | 7.25 | 230 hrs. |
| Ex. 22 | Compound-86 | 3.62 | 814 | 8.14 | 7.07 | 241 hrs. |
| Com. Ex. 1 | HTM-1 | 3.62 | 722 | 7.22 | 6.27 | 121 hrs. |
| Com. Ex. 2 | HTN-2 | 3.66 | 764 | 7.65 | 6.56 | 165 hrs. |

In Table 3, when Examples 13 to 22 were compared with Comparative Examples 1 and 2, while the organic EL devices of Comparative Examples 1 and 2 had light emission efficiencies of 7.22 and 7.65 cd/A, respectively, when a current with a current density of 10 mA/cm² was passed therethrough, the organic EL devices of Examples 13 to 22 had light emission efficiencies of 8.00 to 8.38 cd/A and therefore exhibited higher efficiency. Moreover, with regard to power efficiency as well, while the organic EL devices of Comparative Examples 1 and 2 had power efficiencies of 6.27 and 6.56 lm/W, respectively, the organic EL devices of Examples 13 to 22 had power efficiencies of 6.93 to 7.25 lm/W and therefore exhibited higher efficiency. Furthermore, with regard to device lifespan (at a decay of 95%), while the organic EL devices of Comparative Examples 1 and 2 had device lifespans of 121 and 165 hours, respectively, the organic EL devices of Examples 13 to 22 had device lifespans of 230 to 257 hours, from which it can be seen that the device lifespan was increased.

It was found that, in each organic EL device of the present invention, since the compound having a specific triarylamine structure was chosen as the material of the electron blocking layer, the carrier balance in the organic EL device was improved, and therefore, higher light emission efficiency and a longer lifespan were realized compared with a conventional organic EL device.

The compound having a triarylamine structure of the present invention can also be expected to achieve similar effects when used as a constituent material of a hole injection layer, a hole transport layer, or a light emitting layer.

INDUSTRIAL APPLICABILITY

An organic EL device of the present invention in which a compound having a specific triarylamine structure is used has increased light emission efficiency and also improved durability. Therefore, the organic EL device of the present invention can be applied to a wide variety of uses such as home electric appliances and lighting equipment, for example.

LIST OF REFERENCE NUMERALS

1 Glass Substrate
2 Anode
3 Hole Injection Layer
4 Hole Transport Layer
5 Electron Blocking Layer
6 Light Emitting Layer
7 Electron Transport Layer
8 Electron Injection Layer
9 Cathode

The invention claimed is:

1. A compound having a triarylamine structure and being represented by the structural formula (A-1) below:

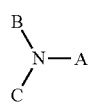

(A-1)

where A represents a group having the structural formula (B-3) below, B, and C may be the same or different, and each represents a substituted or unsubstituted phenyl group, or a substituted or unsubstituted fused polycyclic aromatic group:

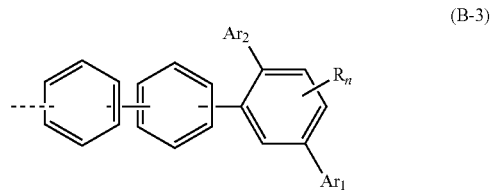

(B-3)

where the dashed line portion represents a binding site;

R represents a hydrogen atom, a heavy hydrogen atom, a fluorine atom, a chlorine atom, a cyano group, a nitro group, a linear or branched alkyl group having 1 to 6 carbon atoms and optionally having a substituent, a cycloalkyl group having 5 to 10 carbon atoms and optionally having a substituent, a linear or branched alkenyl group having 2 to 6 carbon atoms and optionally having a substituent, a linear or branched alkyloxy group having 1 to 6 carbon atoms and optionally having a substituent, a cycloalkyloxy group having 5 to 10 carbon atoms and optionally having a substituent, a substituted or unsubstituted aromatic heterocyclic group, a substituted or unsubstituted aromatic hydrocarbon group, a substituted or unsubstituted fused polycyclic aromatic group, or a substituted or unsubstituted aryloxy group; n is the number of Rs and represents an integer of 0; and $Ar_1$ and $Ar_2$ may be the same or different, and each represent a substituted or unsubstituted aromatic hydrocarbon group, a substituted or unsubstituted aromatic heterocyclic group, or a substituted or unsubstituted fused polycyclic aromatic group, with the proviso that $Ar_1$ and $Ar_2$ are not a dibenzofuranyl group or a dibenzothienyl group.

2. The compound having a triarylamine structure according to claim 1, wherein the group represented by the structural formula (B-3) is a group represented by the structural formula (B-6) below:

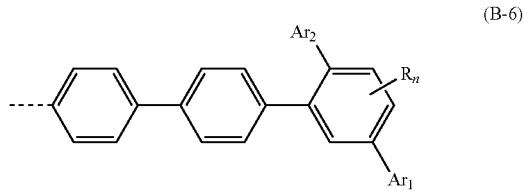

(B-6)

where $Ar_1$, $Ar_2$, n, and R are as defined in the structural formula (B-3).

3. An organic EL device comprising a pair of electrodes and one or more organic layers sandwiched therebetween, wherein the compound having a triarylamine structure according to claim 1 is used as a constituent material of at least one of the organic layers.

4. The organic EL device according to claim 3, wherein the at least one organic layer is a hole transport layer.

5. The organic EL device according to claim 3, wherein the at least one organic layer is an electron blocking layer.

6. The organic EL device according to claim 3, wherein the at least one organic layer is a hole injection layer.

7. The organic EL device according to claim 3, wherein the at least one organic layer is a light emitting layer.

* * * * *